US008853390B2

(12) United States Patent
Ku et al.

(10) Patent No.: US 8,853,390 B2
(45) Date of Patent: Oct. 7, 2014

(54) PROCESSES FOR PREPARING 1,2-SUBSTITUTED CYCLOPROPYL DERIVATIVES

(75) Inventors: Yi-Yin Ku, Buffalo Grove, IL (US); Timothy A. Grieme, Chicago, IL (US); Jeffrey M. Kallemeyn, Libertyville, IL (US); Mathew M. Mulhern, Lake Villa, IL (US)

(73) Assignee: AbbVie Inc., North Chicago, IL (US)

( * ) Notice: Subject to any disclaimer, the term of this patent is extended or adjusted under 35 U.S.C. 154(b) by 98 days.

(21) Appl. No.: 13/232,751

(22) Filed: Sep. 14, 2011

(65) Prior Publication Data

US 2012/0071651 A1    Mar. 22, 2012

Related U.S. Application Data

(60) Provisional application No. 61/397,705, filed on Sep. 16, 2010.

(51) Int. Cl.
*C07D 207/06* (2006.01)
*C07D 401/10* (2006.01)
*C07D 403/10* (2006.01)
*C07D 495/04* (2006.01)

(52) U.S. Cl.
USPC ........... 544/114; 544/176; 544/106; 544/224; 544/238; 548/578; 548/539; 546/226; 546/161; 546/192

(58) Field of Classification Search
USPC .......... 544/114, 176, 106, 224, 238; 548/578, 548/539; 546/226, 161, 192
See application file for complete search history.

(56) References Cited

U.S. PATENT DOCUMENTS

| 4,507,318 | A  | 3/1985  | Cousse et al.    |
| 5,086,054 | A  | 2/1992  | Parish           |
| 6,048,876 | A  | 4/2000  | Annoura et al.   |
| 6,166,023 | A  | 12/2000 | Schindler et al. |
| 6,235,791 | B1 | 5/2001  | Breliere et al.  |
| 6,515,013 | B2 | 2/2003  | Bennani et al.   |
| 6,620,839 | B2 | 9/2003  | Bennani et al.   |
| 6,838,466 | B2 | 1/2005  | Zhu et al.       |
| 6,969,730 | B2 | 11/2005 | Cowart et al.    |
| 7,094,790 | B2 | 8/2006  | Cowart et al.    |
| 7,098,222 | B2 | 8/2006  | Altenbach et al. |
| 7,153,889 | B2 | 12/2006 | Altenbach et al. |
| 7,205,316 | B2 | 4/2007  | Altenbach et al. |
| 7,345,034 | B2 | 3/2008  | Zhao et al.      |
| 7,358,263 | B2 | 4/2008  | Cowart et al.    |
| 7,381,537 | B2 | 6/2008  | Demuth et al.    |
| 7,462,599 | B2 | 12/2008 | Schilling et al. |
| 7,576,110 | B2 | 8/2009  | Cowart et al.    |
| 7,696,193 | B2 | 4/2010  | Sehmi et al.     |
| 7,732,162 | B2 | 6/2010  | Hoffman et al.   |
| 7,799,773 | B2 | 9/2010  | Bamford et al.   |

| 2002/0052383 | A1 | 5/2002  | Bakthavatchalam et al. |
| 2002/0138210 | A1 | 9/2002  | Wilkes et al.          |
| 2002/0169188 | A1 | 11/2002 | Cowart et al.          |
| 2003/0119796 | A1 | 6/2003  | Strony                 |
| 2004/0224954 | A1 | 11/2004 | Sattlegger et al.      |
| 2004/0224980 | A1 | 11/2004 | Sattlegger et al.      |
| 2005/0171181 | A1 | 8/2005  | Wager et al.           |
| 2005/0182045 | A1 | 8/2005  | Nagase et al.          |
| 2005/0245529 | A1 | 11/2005 | Stenkamp et al.        |
| 2006/0040918 | A1 | 2/2006  | Bamford et al.         |
| 2006/0074103 | A1 | 4/2006  | Corte et al.           |
| 2007/0066588 | A1 | 3/2007  | Cowart et al.          |
| 2007/0066644 | A1 | 3/2007  | De Lera Ruiz et al.    |
| 2007/0066821 | A1 | 3/2007  | Allison et al.         |
| 2007/0078133 | A1 | 4/2007  | Liu et al.             |
| 2007/0208005 | A1 | 9/2007  | Parr et al.            |
| 2007/0299056 | A1 | 12/2007 | Bamford et al.         |
| 2008/0021081 | A1 | 1/2008  | Liu et al.             |
| 2008/0027041 | A1 | 1/2008  | Hudkins et al.         |
| 2008/0139589 | A1 | 6/2008  | Kanatani et al.        |
| 2008/0176925 | A1 | 7/2008  | Butler et al.          |
| 2008/0242653 | A1 | 10/2008 | Liu et al.             |
| 2008/0286810 | A1 | 11/2008 | Demuth et al.          |
| 2009/0036425 | A1 | 2/2009  | Dow et al.             |
| 2009/0068699 | A1 | 3/2009  | Schilling et al.       |
| 2009/0075938 | A1 | 3/2009  | Wynne et al.           |
| 2009/0076020 | A1 | 3/2009  | Arnold et al.          |
| 2009/0137587 | A1 | 5/2009  | Naya et al.            |

(Continued)

FOREIGN PATENT DOCUMENTS

CA    2734800 A1    2/2010
DE    10153345 A1   5/2003

(Continued)

OTHER PUBLICATIONS

Airaksinen M.S., et al., "Histamine Neurons in Human Hypothalamus: Anatomy in Normal and Alzheimer Diseased Brains," Neuroscience, 1991, vol. 44 (2), pp. 465-481.
Arrang J.M., et al., "Auto-inhibition Of Brain Histamine Release Mediated by a Novel Class ($H_3$) of Histamine Receptor," Nature, 1983, vol. 302, pp. 832-837.
Arrang J.M., et al., "Highly Potent and Selective Ligands for Histamine $H_3$-Receptors," Nature, 1987, vol. 327, pp. 117-123.
Arrang J.M., et al., "Histamine $H_3$ Receptor Binding Sites in Rat Brain Membranes:Modulations by Guanine Nucleotides and Divalent Cations," European Journal of Pharmacology, 1990, vol. 188, pp. 219-227.
Barbier A.J., et al., "Acute Wake-Promoting Actions of JNJ-5207852, a Novel, Diamine-based $H_3$ Antagonist," British Journal of Pharmacology, 2004, vol. 143, pp. 649-661.
Barbier A.J., et al., "Histaminergic Control of Sleep-Wake Cycles: Recent Therapeutic Advances for Sleep and Wake Disorders ," CNS and Neurological Disorders-Drug Targets, 2007, vol. 6, pp. 31-43.

(Continued)

*Primary Examiner* — Kahsay Habte
(74) *Attorney, Agent, or Firm* — Lisa V. Mueller; Michael Best & Friedrich LLP

(57) ABSTRACT

The present invention relates to processes for preparing enantiomerically pure cyclopropyl amine derivatives and salts thereof; the chiral intermediates such as the chiral salts are useful for the preparation of such chiral compounds and salts; pharmaceutical compositions comprising the compounds and salts; and method of using such compositions. The chiral cyclopropyl amine derivatives are useful for binding to histamine $H_3$ receptor sites and for providing therapeutic agents for histamine $H_3$ mediated disease.

16 Claims, No Drawings

(56) References Cited

U.S. PATENT DOCUMENTS

| | | |
|---|---|---|
| 2009/0192168 A1 | 7/2009 | Muci et al. |
| 2010/0016344 A1 | 1/2010 | Wakefield et al. |
| 2010/0040575 A1 | 2/2010 | Hoffmann et al. |
| 2010/0204205 A1 | 8/2010 | Barak et al. |
| 2010/0216812 A1 | 8/2010 | Griffin |
| 2010/0227876 A1 | 9/2010 | Rech |
| 2010/0249144 A1 | 9/2010 | Demong et al. |
| 2010/0267714 A1 | 10/2010 | Jorgensen et al. |
| 2010/0273778 A1 | 10/2010 | Cowart et al. |
| 2010/0286160 A1 | 11/2010 | Gilbert et al. |
| 2010/0292188 A1 | 11/2010 | Denonne et al. |
| 2011/0009430 A1 | 1/2011 | Moran et al. |
| 2011/0098300 A1 | 4/2011 | Celanire et al. |
| 2011/0195932 A1 | 8/2011 | Wynne et al. |
| 2012/0071651 A1 | 3/2012 | Ku et al. |

FOREIGN PATENT DOCUMENTS

| | | |
|---|---|---|
| DE | 10153347 A1 | 5/2003 |
| EP | 188887 A1 | 7/1986 |
| EP | 188887 A1 * | 7/1986 |
| EP | 251466 A2 | 1/1988 |
| EP | 0668270 A2 | 8/1995 |
| EP | 1321169 A1 | 6/2003 |
| EP | 1595881 A1 | 11/2005 |
| EP | 1675578 A2 | 7/2006 |
| EP | 1961416 A1 | 8/2008 |
| EP | 2117540 A1 | 11/2009 |
| EP | 2195293 A2 | 6/2010 |
| EP | 2206496 A1 | 7/2010 |
| EP | 2238144 A1 | 10/2010 |
| EP | 2253615 A1 | 11/2010 |
| EP | 2289498 A1 | 3/2011 |
| EP | 2300426 A1 | 3/2011 |
| FR | 2856596 A1 | 12/2004 |
| GB | 1086191 A | 10/1967 |
| GB | 2210364 A | 6/1989 |
| JP | 2000047358 A | 2/2000 |
| JP | 2002236340 A | 8/2002 |
| JP | 2005170934 A | 6/2005 |
| JP | 2005281223 A | 10/2005 |
| NL | 6412766 A | 5/1965 |
| WO | WO-0042023 A1 | 7/2000 |
| WO | WO-0044728 A1 | 8/2000 |
| WO | WO-0063208 A1 | 10/2000 |
| WO | WO-0064884 A1 | 11/2000 |
| WO | WO-0213821 A1 | 2/2002 |
| WO | WO-0244128 A2 | 6/2002 |
| WO | WO-03066604 A2 | 8/2003 |
| WO | WO-03099276 A1 | 12/2003 |
| WO | WO-03104235 A1 | 12/2003 |
| WO | WO-2004026305 A1 | 4/2004 |
| WO | WO-2004035556 A1 | 4/2004 |
| WO | WO-2004037801 A1 | 5/2004 |
| WO | WO-2004037813 A1 | 5/2004 |
| WO | WO-2004041776 A2 | 5/2004 |
| WO | WO-2004046110 A1 | 6/2004 |
| WO | WO-2004056369 A1 | 7/2004 |
| WO | WO-2004098625 A2 | 11/2004 |
| WO | WO-2004099199 A1 | 11/2004 |
| WO | WO-2004101546 A1 | 11/2004 |
| WO | WO-2005000315 A1 | 1/2005 |
| WO | WO-2005009471 A1 | 2/2005 |
| WO | WO-2005009976 A1 | 2/2005 |
| WO | WO-2005018045 A1 | 2/2005 |
| WO | WO-2005032468 A2 | 4/2005 |
| WO | WO-2005058837 A1 | 6/2005 |
| WO | WO-2005072740 A2 | 8/2005 |
| WO | WO-2005080361 A1 | 9/2005 |
| WO | WO-2005087746 A1 | 9/2005 |
| WO | WO-2005103032 A2 | 11/2005 |
| WO | WO-2005108384 A1 | 11/2005 |
| WO | WO-2005123723 A1 | 12/2005 |
| WO | WO-2006004937 A2 | 1/2006 |
| WO | WO-2006018260 A1 | 2/2006 |
| WO | WO-2006029906 A1 | 3/2006 |
| WO | WO-2006040192 A1 | 4/2006 |
| WO | WO-2006061193 A1 | 6/2006 |
| WO | WO-2006072596 A1 | 7/2006 |
| WO | WO-2006085692 A1 | 8/2006 |
| WO | WO-2006090142 A1 | 8/2006 |
| WO | WO-2006097691 A1 | 9/2006 |
| WO | WO-2006103537 A2 | 10/2006 |
| WO | WO-2006103546 A2 | 10/2006 |
| WO | WO-2006090142 C2 | 11/2006 |
| WO | WO-2006123020 A1 | 11/2006 |
| WO | WO-2006124687 A1 | 11/2006 |
| WO | WO-2006132424 A1 | 12/2006 |
| WO | WO-2006132914 A2 | 12/2006 |
| WO | WO-2007003604 A2 | 1/2007 |
| WO | WO-2007004735 A1 | 1/2007 |
| WO | WO-2006132914 A3 | 3/2007 |
| WO | WO-2007024004 A1 | 3/2007 |
| WO | WO-2007025144 A1 | 3/2007 |
| WO | WO-2007025596 A1 | 3/2007 |
| WO | WO-2007038074 A1 | 4/2007 |
| WO | WO-2007048595 A1 | 5/2007 |
| WO | WO-2007052124 A1 | 5/2007 |
| WO | WO-2007126957 A2 | 11/2007 |
| WO | WO-2007137968 A1 | 12/2007 |
| WO | WO-2007150010 A2 | 12/2007 |
| WO | WO 2007150010 A2 * | 12/2007 |
| WO | WO-2008064310 A2 | 5/2008 |
| WO | WO-2008064317 A1 | 5/2008 |
| WO | WO-2008064318 A2 | 5/2008 |
| WO | WO-2008067257 A2 | 6/2008 |
| WO | WO-2008104590 A2 | 9/2008 |
| WO | WO-2008151156 A1 | 12/2008 |
| WO | WO-2009024823 A2 | 2/2009 |
| WO | WO-2009030716 A1 | 3/2009 |
| WO | WO-2009039431 A2 | 3/2009 |
| WO | WO-2009081195 A1 | 7/2009 |
| WO | WO-2009085945 A1 | 7/2009 |
| WO | WO-2009092764 A1 | 7/2009 |
| WO | WO-2009100120 A2 | 8/2009 |
| WO | WO-2009100294 A2 | 8/2009 |
| WO | WO-2009115874 A2 | 9/2009 |
| WO | WO-2009124553 A2 | 10/2009 |
| WO | WO-2009147149 A1 | 12/2009 |
| WO | WO-2009151991 A1 | 12/2009 |
| WO | WO-2010007382 A1 | 1/2010 |
| WO | WO-2010071822 A1 | 6/2010 |
| WO | WO-2010080757 A2 | 7/2010 |
| WO | WO-2010129242 A2 | 11/2010 |
| WO | WO-2011083314 A1 | 7/2011 |
| WO | WO-2011083315 A1 | 7/2011 |
| WO | WO-2011083316 A1 | 7/2011 |

OTHER PUBLICATIONS

Berlin M., et al., "Histamine H3 Receptor as a Drug Discovery Target," Journal of Medicinal Chemistry, 2011, vol. 54 (1), pp. 26-53.
Berlin M., et al., "Recent Advances in the Development of Histamine H3 Antagonists," Expert Opinion in the Therapeutic Patents, 2007, vol. 17 (6), pp. 675-687.
Bernaerts P., et al., "Histamine H3 Antagonist Thioperamide Dose-Dependently Enhances Memory Consolidation and Reverse Amnesia Induced by Dizocilpine or Scopolamine in a One-Trail Inhibitory Avoidance Task in Mice," Behavioural Brain Research, 2004, vol. 154, pp. 211-219.
Bjenning C., et al., "Peripherally Administered Ciproxifan Elevates Hypothalamic Histamine levels and Potently Reduces Food Intake in the Sprague Dawley Rat" in: Histamine Research in the New Mellennium, Watanabe T., et al., eds., Elsevier Science, 2001, pp. 449-450.
Blandina P., et al., "Histamine Neuronal System as a Therapeutic Target for the Treatment of Cognitive Disorders," Future Neurology, 2010, vol. 5 (4), pp. 543-555.
Browman K.E. et al., "Enhancement of Prepulse Inhibition of Startle in Mice by the H3 Receptor Antagonists Thioperamide and Ciproxifan," Behavioiral Brain Research, 2004m vol. 153 (1), pp. 69-76.

(56) References Cited

OTHER PUBLICATIONS

Burger A., et al., "2-(4-imidazolul)cyclopropylamine," Journal of Medicinal Chemistry, 1970, vol. 13, pp. 33-35.
Celanire S., et al., "Keynote Review: Histamine H3 Receptor Antagonists Reach Out for The Clinic," Drug Discovery Today, 2005, vol. 10 (23/24), pp. 1613-1627.
Charette A.B. et al., "(2S,3S)-(+)-(3-Phenylcyclopropyl)Methanol," Org Syntheses Coll, 1999, vol. 76, pp. 86-96.
Chen Z., et al., "Effects of Histamine on MK-801-induced Memory Deficits in Radial Maze Performance in Rats," Brain Research, 1999, vol. 839, pp. 186-189.
Chen Z., et al., "Pharmacological Effects of Carcinine on Histaminergic Neurons in the Brain," British Journal of Pharmacology, 2004, vol. 143, pp. 573-580.
Clapham J., et al., "Thioperamide, the Selective Histamine H3 Receptor Antagonist, Attenuates Stimulant Induced Locomotor Acitivity in the Mouse," European Jounal of Pharmacology, 1994, vol. 259 (2), pp. 107-114.
Collins S.D., "Emerging Therapies for Neuropathic Pain," Expert Opinion on Emerging Drugs, 2005, vol. 10 (1), pp. 95-108.
Cowart M., et al., "4-(2-[2-(2(R)- Methylpyrrolidin-1-yl) ethyl] Benzofuran-5yl) Benzonitrile and Related 2-Aminoethylbenzofuran H3 Receptor Antagonists Potently Enhance Cognition and Attention," Journal of Medicinal Chemistry, 2005, vol. 48 (1), pp. 38-55.
Cowart M., et al., "Pharmacological Characterization of A-960656, a Histamine H3 Receptor Antagonist with Efficacy in Animal Models of Osteoarthritis and Neuropathic Pain," European Journal of Pharmacology, 2012, vol. 684 (1-3), pp. 87-94.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
De Almeida M.A., et al., "Memory Facilitation by Histamine," Archives Internationales De Physiologie Et De Biochimie, 1986, vol. 283 (2), pp. 193-198.
Delaunois A., et al., "Modulation of Acetylcholine, Capsaicin and subsztance P Effects by Histamine $H_3$ Receptors in Isolated Perfused Rabbit Lungs," European Journal of Pharmacology, 1995, vol. 277 (2-3), pp. 243-250.
Dimitriadou V., et al., "Functional Relationship Between Mast Cells and C-Sensitive Nerve Fibres Evidenced by Histamine $H_3$ -Receptor Modulation in Rat Lung and Spleen," Clinical Science, 1994, vol. 87, pp. 151-163.
Dray A., et al., "Pharmacology of Chronic Pain," Trends in Pharmacological Sciences, 1994, vol. 15 (6), pp. 190-197.
Dray et al., "Arthritis Pain. Future Targets to Control Osteoarthritis Pain," Arthritis Research and Therapy, 2007, vol. 9 (3), pp. 212.
Dumery V., et al., "Development of Amygdaloid Cholinergic Mediation of Passive Avoidance Learning in the Rat," Experimental Brain Research , 1987, vol. 67(1), pp. 61-69.
Dvorak C.A., et al., "4-Phenoxypiperidines: Potent, Conformationally Restricted, non-Imidazole Histamine H3 Antagonists," Journal of Medicinal Chemistry, 2005, vol. 48 (6), pp. 2229-2238.
Dworkin R.H., "An Overview of Neuropathic Pain: Syndromes, Symptoms, Signs, and Several Mechanisms," Clinical Journal of Pain, 2002, vol. 18 (6), pp. 343-349.
Esbenshade T.A., et al., "Histamine H3 Receptor Antagonists: Preclinical Promise for Treating Obesity and Cognitive Disorders," Molecular Interventions, 2006, vol. 6 (2), pp. 77-88.
Esbenshade T.A., et al., "Pharmacological and Behavioral Properties of A-349821, a Selective and Potent Human Histamine H3 Receptor Antagonist," Biochemical Pharmacology, 2004, vol. 68 (5), pp. 933-945.
Esbenshade T.A., et al., "Pharmacological Properties of ABT-239 [4-(2- {2-[(2R)-2-Methylpyrrolidinyl]ethyl}-benzofuran-5-yObenzonitrile]: I. Potent and Selective Histamine H3 Receptor Antagonist with Drug-Like Properties," Journal of Pharmacology and Experimental Therapeutics, 2005, vol. 313 (1), pp. 165-175.

Esbenshade T.A., et al., "The Histamine H3 Receptor: An Attractive Target for the Treatment of Cognitive Disorders," British Journal of Pharmacology, 2008, vol. 154 (6), pp. 1166-1181.
Fernihough J., et al., "Pain Related Behaviour in Two Models of Osteoarthritis in the Rat Knee," Pain, 2004, vol. 112 (1-2), pp. 83-93.
Final Office Action mailed Aug. 8, 2011 for U.S. Appl. No. 11/766,987, filed Jun. 22, 2007.
Fitzsimons C., et al., "Histamine Receptors Signaling in Epidermal Tumor Cell Lines with H-Ras Gene Alterations," Inflammation Research, 1998, vol. 47 (1), pp. S50-S51.
Foley A.G., et al., "H3 Receptor Antagonism Enhances NCAM PSA-Mediated Plasticity and Improves Memory Consolidation in Odor Discrimination and Delayed Match-to-Position Paradigms," Neuropsychopharmacology, 2009, vol. 34 (12), pp. 2585-2600.
Fox G.B., et al., "Effects of Histamine H3 Receptor Ligands GT2331 and Ciproxifan in a Repeated Acquisition Response in the Spontaneously Hypertensive Rat Pup," Behavioural Brain Research, 2002, vol. 131 (1-2), pp. 151-161.
Fox G.B., et al., "Identification of Novel H3 Receptor (H3R) Antagonists with Cognition Enhancing Properties in Rats," Inflammation Research, 2003, vol. 52 (1), pp. S31-S32.
Fox G.B., et al., "Pharmacological Properties of ABT-239 [4-(2-{2-[(2R)-2-Methylpyrrolidinty]ethyl}-benzofuran-5-yhbenzonitrile]- : II Neurophysiological Characterization and Broad Preclinical Efficacy in Cognition and Schizophrenia of a Potent and Selective Histamine H3 R," Journal of Pharmacology and Experimental Therapeutics, 2005, vol. 313 (1), pp. 176-190.
Fox G.B., et al., "Two Novel and Selective Nonimidazole H3 Receptor Antagonists A-304121 and A-317920: II. In Vivo Behavioral and Neurophysiological Characterization," Journal of Pharmacology and Experimental Therapeutics, 2003, vol. 305 (3), pp. 897-908.
Furniss B.S., et al., Vogel's Textbook of Practical Organic Chemistry, 5th Edition, Longman Scientific & Technical, 1989, Table of Contents.
Glase S.A., et al., "Attention Deficit Hyperactivity Disorder: Pathophysiology and Design of New Treatments," Annual Reports in Medicinal Chemistry, 2002, vol. 37, pp. 11-20.
Haas L., et al., "Subcortical Modulation of Synaptic Plasticity in the Hippocampus," Behavioural Brain Research, 1995, vol. 66 (1-2), pp. 41-44.
Halpern, M.T., "GT-2331," Current Opinion in Central and Peripheral Nervous System Investigational Drugs, vol. 1, pp. 524-527, 1999.
Hancock A.A., et al., "Antiobesity Effects of A-331440, a Novel Non-Imidazole Histamine H3 Receptor Antagonist," European Journal of Pharmacology, 2004, vol. 487 (1-3), pp. 183-197.
Hancock A.A., et al., "Histamine H3 Antagonists in Models of Obesity," Inflammatory Research, 2004, vol. 53 (Suppl. 1), pp. S47-S48.
Harada C., et al., "Inhibitory Effect of Iodophenpropit, a Selective Histamine H3 Antagonist, on Amygdaloid Kindled Seizures," Brain Research Bulletin, 2004, vol. 63 (2), pp. 143-146.
Harada C., et al., "Intracerebroventricular Administration of Histamine H3 Receptor Antagonists Decreases Seizures in Ray Models of Epilepsia," Methods and Findings in Experimental and Clinical Pharmacology, 2004, vol. 26 (4), pp. 263-270.
Hriscu A., et al., "Experimental Evaluation of the Analgesic Efficacy of Some Antihistamines as Proof of the Histaminergic Receptor Involvement in Pain," Famacia, 2001, vol. 49 (2), pp. 23-30.
Hsieh G.C., et al., "The Histamine H3 Receptor as a Potential Antinociceptive Target: Effects of Selective H3 Antagonists in Several Preclinical Pain Models and the Involvement of Noradrenergic Systems," Global Pharmaceutical Research & Development, 2009, Abbott Laboratories, Abbott Park, IL 60064.
Huang Y.W., et al., "Effect of the Histamine $H_3$-antagonist Clobenpropit on Spatial Memory Deficits Induced by MK-801 as Evaluated by Radial Maze in Sprague-Dawley Rats," Behavioural Brain Research, 2004, vol. 151 (1-2), pp. 287-293.
International Search Report for Application No. PCT/DK2003/000071, mailed on Jul. 29, 2003, 10 pages.
International Search Report for Application No. PCT/EP2006/063753, mailed on Apr. 27, 2007, 11 pages.
International Search Report for Application No. PCT/EP2008/052430, mailed on May 25, 2009, 5 pages.

(56) References Cited

OTHER PUBLICATIONS

International Search Report for Application No. PCT/US2007/071849, mailed on Jan. 29, 2008, 4 pages.
International Search Report for Application No. PCT/US2008/077103, mailed on Apr. 27, 2009, 3 pages.
International Search Report for Application No. PCT/US2008/085622, mailed on Jun. 8, 2009, 6 pages.
International Search Report for Application No. PCT/US2008/085662, mailed on Jun. 8, 2009, 4 pages.
International Search Report for Application No. PCT/US2009/033062, mailed on Sep. 1, 2009, 4 pages.
International Search Report for Application No. PCT/US2009/033329, mailed on Sep. 17, 2009, 3 pages.
International Search Report for Application No. PCT/US2010/032488, mailed on Nov. 2, 2010, 11 pages.
International Search Report for Application No. PCT/US2011/051603, mailed on Dec. 5, 2011, 5 pages.
Itoh E., et al., "Thioperamide, A Histamine $H_3$ Receptor Antagonist, Powerfully Suppresses Peptide YY-Induced Food Intake in Rats," Biological Psychiatry, 1999, vol. 45 (4), pp. 475-481.
Jantzen, et al., Modern Pharmacueticals, 1996, pp. 596.
Joshi S.K., et al., "Animal Models of Pain for Drug Discovery," Expert Opinion on Drug Discovery, 2006, vol. 1 (4), pp. 341-352.
Kallemeyn J.M., et al., "Asymmetric Synthesis of Di- and Trisubstituted Cyclopropanes Through an Intramolecular Ring Closure," Synlett, 2011, vol. 4, pp. 535-538.
Kallemeyn J.M., et al., ChemInform, 2011, vol. 42 (26), 4 pages.
Komater V.A., et al., "H3 Receptor Blockade by Thioperamide Enhances Cognition in Rats without Inducing Locomotor Sensitization," Psychopharmacology, 2003, vol. 167 (4), pp. 363-372.
Krueger K.M., et al., "G Protein-Dependent Pharmacology of Histamine H3 Receptor Ligands: Evidence for Heterogeneous Active State Receptor Conformations," Journal of Pharmacology and Experimental Therapeutics, 2005, vol. 314 (1), pp. 271-281.
Leurs R., et al., eds., "The Histamine H3 Receptor: A Target for New Drugs," vol. 30, Elsevier Science B.V., 1998, Table of Contents.
Leurs R., et al., "En Route to New Blockbuster Anti-Histamines: Surveying the Offspring of the Expanding Histamine Receptor Family," Trends in Pharmacological Sciences, 2011, vol. 32 (4), pp. 250-257.
Leurs R., et al., "Histamine Homologues Discriminating between Two Functional $H_3$ Receptor Assays. Evidence for $H_3$ Receptor," Journal of Pharmacology and Experimental Therapeutics, 1996, vol. 276 (3), pp. 1009-1015.
Leurs R., et al., The Histamine H3-Receptor: A Target For Developing New Drugs, Elsevier Science, 1998, vol. 39, pp. 127-165.
Leurs R., et al., "The Medicinal Chemistry And Therapeutic Potentials Of Ligands Of The Histamine $H_3$ Receptor," Progress In Drug Research, 1995, vol. 45, pp. 107-165.
Ligneau X., et al., "Neurochemical and Behavioral Effects of Ciproxifan, a Potent Histamine H3-Receptor Antagonist," Journal of Pharmaceutical and Experimental Therapeutics, 1998, vol. 287 (2), pp. 658-666.
Lin J.S., et al., "Involvement of Histaminergic Neurons in Arousal Mechanisms Demonstrated with $H_3$-Receptor Ligands in the Cat," 1990, vol. 523 (2), pp. 325-330.
Lozada A.F., et al., "Plasticity of Histamine $H_3$ Receptor Expression and Binding in the Vestibular Nuclei After Labyrinthectomy in Rat," Biomedical Center Neuroscience, 2004, vol. 5, pp. 32.
Malmberg Aiello P., et al., "Role of Histamine in Rodent Antinociception," British Journal of Pharmacology, 1994, vol. 111 (4), pp. 1269-1279.
Mazurkiewicz-Kwilecki I.M., et al., "Changes in the Regional Brain Histamine and Histidine Levels in Postmortem Brains of Alzheimer Patients," Canadian Journal of Physiology and Pharmacology, 1989, vol. 67 (1), pp. 75-78.
McLeod R.L., et al., "Combined Histamine H1 and H3 Receptor Blockade Produces Nasal Decongestion in an Experimental Model of Nasal Congestion," American Journal of Rhinology, 1999, vol. 13 (5), pp. 391-399.
McLeod R.L., et al., "Histamine $H_3$ Antagonists," Progress in Respiratory Research, 2001, vol. 31, pp. 133-136.
Medhurst a.D., et al., "GSK189254, a Novel H3 Receptor Antagonist that Binds to Histamine H3 Receptors in Alzheimer's Disease Brain and Improves Cognitive Performance in Preclinical Models," Journal of Pharmacology and Experimental Therapeutics, 2007, vol. 321 (3), pp. 1032-1045.
Medhurst A.D., et al., "Structually Novel Histamine H3 Receptor Antagonists GSK207040 Secondary Allodynia in Rats," Biochemical Pharmacology, 2007, vol. 73, pp. 1182-1194.
Medhurst S.J., et al., "Novel histamine H3 receptor antagonists GSK189254 and GSK334429 are efficacious in surgically-induced and virally-induced rat models of neuropathic pain," Pain, 2008, vol. 138 (1), pp. 61-69.
Meguro K., et al., "Effects of Thioperamide, a Histamine H3 Antagonist, on the Step-Through Passive Avoidance Response and Histidine Decarboxylase Activity in Senescence-Accelerated Mice," Pharmacology, Biochemistry and Behavior, 1995, vol. 50 (3), pp. 321-325.
Monti J., et al., "Sleep and Waking During Acute Histamine $H_3$ Agonist BP2.94 or $H_3$ Antagonist Carboperamide (MR 16155) Administration in Rats," Neuropsychopharmacology, 1996, vol. 15 (1), pp. 31-35.
Morisset S., et al., "Atypical Neuroleptics Enhance Histamine Turnoer in Brain Via 5-Hydroxytryptamino$_2$A Receptor Blockade," Journal Pharmacology and Experimental Therapeutics, 1999, vol. 288 (2), pp. 590-596.
Murakami K., et al., "AQ-0145, A Newly Developed Histamine $H_3$ Antagonist, Decreased Seizure Susceptibility of Electrically Induced Convulsions In Mice," Methods and Findings in Experimental and Clinical Pharmacology, 1995, vol. 17 Suppl C, pp. 70-73.
Njar, "High-Yields Synthesis of Novel Imidazoles and Triazoles form Alcohols and Phenols," Synthesis, 2000, pp. 2019-2028.
Office Action mailed Jan. 7, 2011 for U.S. Appl. No. 11/766,987, filed Jun. 22, 2007.
Office Action mailed Oct. 7, 2010 for U.S. Appl. No. 11/956,816, filed Dec. 14, 2007.
Office Action mailed Sep. 8, 2008 for U.S. Appl. No. 11/766,987, filed Jun. 22, 2007.
Office Action mailed Jan. 9, 2009 for U.S. Appl. No. 11/766,987, filed Jun. 22, 2007.
Office Action mailed Oct. 19, 2009 for U.S. Appl. No. 11/766,987, filed Jun. 22, 2007.
Office Action mailed Mar. 22, 2010 for U.S. Appl. No. 11/956,816, filed Dec. 14, 2007.
O'Neill A.B., et al., "Pharmacological Evaluation of the in Vivo Model of Vestibular Dysfunction in the Rat," Methods and Findings in Experimental and Clinical Pharmacology, 1999, vol. 21 (4), pp. 285-289.
Onodera K., et al., "Improvement by FUB 181, A Novel Histamine H 3-Receptor Antagonist, of Learning and Memory in the Elevated Plus-Maze Test in Mice," Naunyn-Schmiedebergs' Archives of Pharmacology, 1998, vol. 357 (5), pp. 508-513.
Onodera K., et al., "Neuropharmacology of the Histaminergic Neuron System in the Brain And its Relationship with Behavioral Disorders," Progress in Neurobiology, 1994, vol. 42 (6), pp. 685-702.
Pan J.B., et al., "Histaminergic Ligands Attenuate Barrel Rotation in Rats Following Unilateral Labyrinthectomy," Methods and Findings in Experimental and Clinical Pharmacology, 1998, vol. 20 (9), pp. 771-777.
Panula P., et al., "Neuronal Histamine Deficit in Alzheimer's Disease," Neuroscience, 1998, vol. 82 (4), pp. 993-997.
Passani M.B., et al., "Central Histaminergic System and Cognition," Neuroscience and Biobehavioral Reviews, 2000, vol. 24 (1), pp. 107-113.
Penning T.D., et al., "Structure-Activity Relationship Studies on 1-[2-(4-Phenylphenoxy)ethly]pyrrolidine (SC-22716), a Potent Inhibitor of Leukotriene $A_4$ ($LTA_4$) Hydrolase," Journal of Medicinal Chemistry, 2000, vol. 43 (4), pp. 721-735.
Perez-Garcia C., et al., "Effects of Histamine $H_3$ Receptor Ligands in Experimental Models Of Anxiety And Depression," Psychopharmacology, 1999, vol. 142 (2), pp. 215-220.

(56) References Cited

OTHER PUBLICATIONS

Poste G. et al., "Lipid Vesicles as Carriers for Introducing Biologically Active Materials into Cells," Methods in Cell Biology, 1976, vol. 14, pp. 33-71.
Prast H., et al., "Histaminergic Neurons Facilitate Social Memory in Rats," Brain Research, 1996, vol. 734 (1-2), pp. 316-318.
Pu Y.M., et al., "A Facile and Scaleable Synthesis of ABT-239, A Benzofuranoid H3 Antagonist," Organic Process Research and Development, 2005, vol. 9, pp. 45-50.
Roche E.B., ed., Bioreversible Carries in Drug Design Theory and Application, Pergamon Press, 1987, Table of Contents.
Rodrigues A.A., et al., "Interaction of Clozapine with the Histamine H3 Receptor in Rat Brain," British Journal of Pharmacology, 1995, vol. 114 (8), pp. 1523-1524.
Rubin B.R., "Management of Osteoarthritic Knee Pain," Journal of the American Osteopathic Association, 2005, vol. 105 (9 Suppl. 4), pp. S23-S28.
Sakai N., et al., "Effects of Thioperamide, A Histamine H3 Receptor Antagonist, On Locomotor Activity and Brain Histamine Content in Mast Cell-Deficient Wiwv Mice," Life Sciences, 1991, vol. 48 (25), pp. 2397-2404.
Sakata T., et al., "Hypothalamic Neuronal Histamine Modulates Ad Libitum Feeding by Rats," Brain research, 1990, vol. 537 (1-2), pp. 303-306.
Sanchez-Lemus E., et al., "Histamine $H_3$ Receptor Activation Inhibits Dopamine $D_1$ Receptor-Induced Camp Accumulation in Rat Striatal Slices," Neuroscience Letters, 2004, vol. 364 (3), pp. 179-184.
Sander K., et al., "Histamine H3 Receptor Antagonists Go to Clinics," Biological & Pharmaeutical Bulletin, 2008, vol. 31 (12), pp. 2163-2181.
Schwartz J., et al., "Histamine", in: Psychopharmacology: The Fourth Generation Of Progress, Chapter 35, Bloom F.E., et al., eds., Raven Press, 1995, pp. 397-405.
Schweitzer J.B., et al., "Drugs Under Investigation for Attention-Deficit Hyperactivity Disorder," Current Opinion in Investigational Drugs, 2002, vol. 3 (8), pp. 1207-1211.
Shaywitz B.A., et al., "Dopaminergic But Not Noradrenergic Mediation of Hyperactivity and Performance Deficits in the Developing Rat Pup," Psychopharmacology, 1984, vol. 82 (1-2), pp. 73-77.
Smith P.A., et al., "Neuropathic Pain and the Electrophsiology and Pharmacology of Nerve Injury," Drug Development Research, 2001, vol. 54 (3), pp. 140-153.
Szelag A., "Role of Histamine $H_3$ -Receptors in the Proliferation Neoplastic Cells in Vitro," Medical Science Monitor, 1998, vol. 4 (5), pp. 747-755.
Tedford C.E., "Pharmacological Characterization of Gt-2016, A Non-Thiourea-Containing Histamine $H_3$ Antagonist: in Vitro and in Vivo Studies," The Journals Of Pharmacology And Experimental Therapeutics, 1995, vol. 275 (2), pp. 598-604.
Tedford et al., "Cognition and Locomotor Activity in the Developing Rat: Comparisons Of Histamine $H_3$ Receptor Antagonists And ADHD Therapeutics," Society For Neuroscience Abstr, vol. 22, pp. 22, 1996.
Tozer M., et al., "Histamine H3 Receptor Antagonists," Expert Opinion Therapeutic Patents, 2000, vol. 10 (7), pp. 1045-1055.
Vinik A.L., et al., "Diabetic Neuropathies," The Medical Clinics of North America, 2004, vol. 88 (4), pp. 947-999.
Vohora D., et al., "Thioperamide, A Selective Histamine $H_3$ Receptor Antagonist, Protects Against PTZ-Induced Seizures in Mice," Life Sciences, 2000, vol. 66 (22), pp. PL297-PL301.
Wada H., et al., "Is the Histaminergic Neuron System a Regulatory Center for Whole-Brain Activity", Trends in Neurosciences, 1991, vol. 14 (9), pp. 415-418.
Wang Y., et al., "Design and Synthesis of Ether Analogues as Potent and Selective M2 Muscarinic Receptor Antagonists," Bioorganic and Medicinal Chemistry Letters, 2001, vol. 11 (7), pp. 891-894.
Witkin J.M., et al., "Selective Histamine H3 Receptor Antagonists for the Treatment of Cognitive Deficiencies and Other Disorders of the Central Nervous System," Pharmacology and Therapeutics, 2004, vol. 103 (1), pp. 1-20.
Yates, S.L., et al., "Effects of a novel histamine H3 receptor antagonist, GT2394, on food intake and weight gain in Sprague-Dawley rats," Society for Neuroscience, vol. 102 (10), pp. 219, 2000.
Yates S.L., et al., "Identification and Pharmacological Characterization of a Series of New 1H-4-Substituted-Imidazoyl Histamine H3 Receptor Ligands," Journal of Pharmacology and Experimental Therapeutics, 1999, vol. 289 (2), pp. 1151-1159.
Yawata I., et al., "Role Of Histaminergic Neurons in Development of Epileptic Seizures in El Mice," Brain Research. Molecular Brain Research, 2004, vol. 132 (1), pp. 13-17.
Yokoyama H., et al., "Clobenpropit (Vuf-9153), a New Histamine H3 Receptor Antagonist, Inhibits Electrically Induced Convulsions in Mice," European Journal of Pharmacology, 1994, vol. 260 (1), pp. 23-28.
Yokoyama H., et al., "Effect of Thioperamide, a Histamine H3 Receptor Antagonist, on Electrically Induced Convulsions in Mice," Journal of Pharmacology, 1993, vol. 234 (1), pp. 129-133.
Yokoyama H., et al., "Histamine And Seizures Implcations For The Treatment Of Epilepsy," CNS Drugs, 1996, vol. 5 (5), pp. 321-330.
Zhang X., et al., "Trans-1-[(2-Phenylcyclopropyl)methyl]-4-arylpiperazines: Mixed Dopamine D(2)/D(4) Receptor Antagonists as Potential Antipsychotic Agents," Journal of Medicinal Chemistry, 2000, vol. 43 (21), pp. 3923-3932.

* cited by examiner

PROCESSES FOR PREPARING 1,2-SUBSTITUTED CYCLOPROPYL DERIVATIVES

This application claims priority to U.S. Patent Application Ser. No. 61/397,705 filed Sep. 16, 2010, which is incorporated herein by reference.

FIELD OF THE INVENTION

The present invention relates to processes for preparing chiral cyclopropyl amine derivatives and salts thereof; intermediates useful for the preparation of such compounds and salts; pharmaceutical compositions comprising the compounds and salts; and method of using such compositions. The cyclopropyl amine derivatives are useful for binding to histamine $H_3$ receptor sites and for providing therapeutic agents for histamine $H_3$ mediated disease.

BACKGROUND OF THE INVENTION

The chiral 1,2-substituted cyclopropyl carboxylic acid and chiral 1,2-substituted cyclopropyl amide derivatives are intermediate compounds useful for the preparation of chiral cyclopropyl amine derivatives of a general formula:

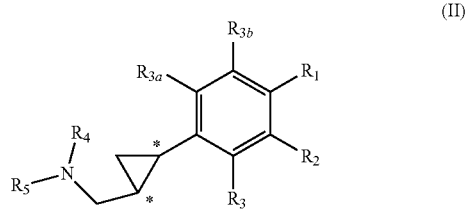

wherein $R_1$, $R_2$, $R_3$, $R_{3a}$, $R_{3b}$, $R_4$, and $R_5$ are as defined below. Compounds of formula (II) are described in WO 2007150010, published on Dec. 27, 2007, corresponding to U.S. patent application Ser. No. 11/766,987, filed on Jun. 22, 2007, and U.S. patent application Ser. No. 11/956,816, filed on Dec. 14, 2007, each of which are all hereby incorporated by reference. The present invention offers a more efficient process to obtain chiral compounds of formula (II) via the chiral resolution of an aryl-cyclopropanecarboxylic acid with chiral amines. The chiral resolution step forms a diasteriomeric chiral salt, which is crystallized to obtain an enantiomerically pure salt. The enantiomerically pure arylcyclopropyl carboxylic acid is obtained upon breaking up the salt. The resulting enantiomerically pure cyclopropyl carboxylic acids can be reacted with various amines to form amides, which can be reduced to form chiral amine derivatives. The intermediate chiral amines can be further coupled with a desired aromatic or heteroaromatic reagent to provide compounds of formula (II).

Compounds of formula (II) have been identified as histamine $H_3$ receptor antagonists. Various histamine $H_3$ receptor antagonists are currently in clinical development for treatment of disease. Diseases for which histamine $H_3$ receptor antagonists are under clinical study include, for example, schizophrenia, cognitive deficits of schizophrenia, Alzheimer's disease, narcolepsy, cataplexy, sleep disorder, hyperalgesia, allergic rhinitis, obesity, attention-deficit hyperactivity disorder, and dementia. Other conditions for which it is believed that histamine $H_3$ receptor ligands can demonstrate therapeutic effect are deficits in attention, diseases with deficits of memory or learning, cognitive deficits and dysfunction in psychiatric disorders, mild cognitive impairment, epilepsy, seizures, and asthma, motion sickness, dizziness, Meniere's disease, vestibular disorders, vertigo, diabetes, type II diabetes, Syndrome X, insulin resistance syndrome, metabolic syndrome, pain, including neuropathic pain, neuropathy, pathological sleepiness, jet lag, drug abuse, mood alteration, bipolar disorder, depression, obsessive compulsive disorder, Tourette's syndrome, Parkinson's disease, and medullary thyroid carcinoma, melanoma, and polycystic ovary syndrome.

It would be beneficial to provide a more practical, economical, and robust processes for preparing the compounds having histamine $H_3$ receptor activity to more efficiently supply histamine $H_3$ receptor antagonist compounds for clinical studies and for eventual commercial supply. It would be particularly beneficial if the process provided the desired chiral compound using environmentally safe reagents under milder reaction conditions.

SUMMARY OF THE INVENTION

In one aspect, the present invention relates to a process for preparing chiral cyclopropyl amine derivatives of formula (II), as described herein.

In another aspect, the present invention relates to a process for preparing the chiral salts of aryl-cyclopropanecarboxylic acid with a chiral amine.

The present invention also is directed to the chiral compounds and salts thereof prepared by the process for preparing chiral salts described above.

The present invention also is directed a chiral aryl-cyclopropanecarboxylic acid salt.

The present invention also is directed to various intermediates useful for preparing chiral compounds of formula (II).

The present invention also is directed to compositions (including pharmaceutical compositions) that comprise compounds of formula (II) or a salt thereof that are prepared by the above processes.

The present invention also is directed to methods of using the compositions of the invention.

Further benefits of Applicants' invention will be apparent to one skilled in the art from reading this patent application.

DETAILED DESCRIPTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

a. Definitions

As used in the specification and the appended claims, unless specified to the contrary, the following terms have the meaning indicated:

The term "aryl" as used herein means a monocyclic hydrocarbon aromatic ring system. Representative examples of aryl include, but are not limited to, phenyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkylcarbonyl, formyl, haloalkoxy, haloalkyl, halogen, hydroxy, hydroxyalkyl, mercapto, nitro, thioalkoxy, $NR_AR_B$, and $(NR_AR_B)$sulfonyl.

The term "heteroaryl", as used herein, refers to an aromatic ring containing one or more heteroatoms independently selected from nitrogen, oxygen, or sulfur, or a tautomer thereof. Such rings can be monocyclic or bicyclic as further described herein. Heteroaryl rings are connected to the parent molecular moiety.

The terms "monocyclic heteroaryl" or "5- or 6-membered heteroaryl ring", as used herein, refer to 5- or 6-membered aromatic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or S atom; one, two, or three N atoms arranged in a suitable manner to provide an aromatic ring; or a ring wherein two carbon atoms in the ring are replaced with one O or S atom and one N atom. Such rings can include, but are not limited to, a six-membered aromatic ring wherein one to four of the ring carbon atoms are replaced by nitrogen atoms, five-membered rings containing a sulfur, oxygen, or nitrogen in the ring; five membered rings containing one to four nitrogen atoms; and five membered rings containing an oxygen or sulfur and one to three nitrogen atoms. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,3]oxadiazolyl, thiazolyl, thienyl, [1,2,3]triazinyl, [1,2,4]triazinyl, [1,3,5]triazinyl, [1,2,3]triazolyl, and [1,2,4]triazolyl.

The term "bicyclic heteroaryl" or "8- to 12-membered bicyclic heteroaryl ring", as used herein, refers to an 8-, 9-, 10-, 11-, or 12-membered bicyclic aromatic ring containing at least 3 double bonds, and wherein the atoms of the ring include one or more heteroatoms independently selected from oxygen, sulfur, and nitrogen. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, thieno[3,2-b]pyridinyl, and pyrrolopyrimidinyl.

Heteroaryl groups of the invention, whether monocyclic or bicyclic, may be substituted with hydrogen, or optionally substituted with one or more substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR_AR_B$, and $(NR_AR_B)$carbonyl. Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the present invention may be present as tautomers.

The terms "heterocyclic ring" and "heterocycle", as used herein, refer to a 4- to 12-membered monocyclic or bicyclic ring containing one, two, three, four, or five heteroatoms independently selected from the group consisting of nitrogen, oxygen, and sulfur and also containing either at least one carbon atom attached to four other atoms or one carbon atom substituted with an oxo group and attached to two other atoms. Four- and five-membered rings may have zero or one double bond. Six-membered rings may have zero, one, or two double bonds. Seven- and eight-membered rings may have zero, one, two, or three double bonds. The non-aromatic heterocycle groups of the invention can be attached through a carbon atom or a nitrogen atom. The non-aromatic heterocycle groups may be present in tautomeric form. Representative examples of nitrogen-containing heterocycles include, but are not limited to, azepanyl, azetidinyl, aziridinyl, azocanyl, dihydropyridazinyl, dihydropyridinyl, dihydropyrimidinyl, morpholinyl, piperazinyl, piperidinyl, pyrrolidinyl, pyrrolinyl, dihydrothiazolyl, dihydropyridinyl, and thiomorpholinyl. Representative examples of non-nitrogen containing non-aromatic heterocycles include, but are not limited to, dioxanyl, dithianyl, tetrahydrofuryl, dihydropyranyl, tetrahydropyranyl, and [1,3]dioxolanyl.

The heterocycles of the invention are substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, amido, arylalkyl, arylalkoxycarbonyl, carboxy, cyano, formyl, haloalkoxy, haloalkyl, halogen, hydroxy, hydroxyalkyl, mercapto, nitro, oxo, thioalkoxy, —$NR_AR_B$, and $(NR_AR_B)$sulfonyl.

Additional examples of heterocycles include, but are not limited to, azetidin-2-one, azepan-2-one, isoindolin-1,3-dione, (Z)-1H-benzo[e][1,4]diazepin-5(4H)-one, pyridazin-3(2H)-one, pyridin-2(1H)-one, pyrimidin-2(1H)-one, pyrimidin-2,4(1H,3H)-dione, pyrrolidin-2-one, benzo[d]thiazol-2(3H)-one, pyridin-4(1H)-one, imidazolidin-2-one, 1H-imidazol-2(3H)-one, piperidin-2-one, tetrahydropyrimidin-2(1H)-one, 1H-benzo[d]imidazol-2(3H)-one, [1,2,4]thiadiazolonyl, [1,2,5]thiadiazolonyl, [1,3,4]thiadiazinonyl, [1,2,4]oxadiazolonyl, [1,2,5]oxadiazolonyl, [1,3,4]oxadiazinonyl, and 1,5-dihydro-benzo[b][1,4]diazepin-2-on-yl.

For the purposes of the application, the term "room temperature" refers to about 25° C. One with skill in the art would understand that room temperature can vary within a few degrees depending on the environment in which any reaction is conducted. For example, temperatures from about 20° C. to about 30° C. are considered to be room temperature.

As used herein, the * denotes a chiral center that can be designated as a R- or S-stereocenter. These stereoisomers are "R" or "S" depending on the configuration of substituents around the chiral carbon atom. The terms "R" and "S" used herein are configurations as defined in the IUPAC 1974 Recommendations for Section E, Fundamental Stereochemistry, Pure Appl. Chem., 1976, 45:13-30.

The term "chiral" refers to a compound that is enantiopure or contains only one of a possible two configurations at a designated stereocenter.

b. Abbreviations

Abbreviations which have been used in the descriptions that follow are: THF for tetrahydrofuran; CDI for 1,1'-carbonyldiimidazole; NaH for sodium hydride; HCl hydrochloric acid; $NaHCO_3$ for sodium bicarbonate; MTBE for methyl t-butyl ether; $BH_3$ for borane; DMSO for dimethylsulfoxide; EtOAc for ethyl acetate; NaOtBu for sodium t-butoxide; and OTf for trifluoromethanesulfonate.

The abbreviation NLT is used to denote "Not Less Than".

The abbreviation KF is used to denote "Karl Fischer".

c. Description of Present Invention

In one aspect, the present invention relates to a process for preparing a chiral compound of formula:

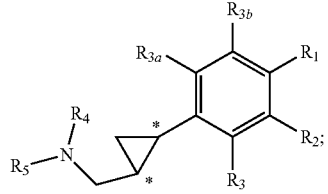

(II)

wherein $R_2$, $R_3$, $R_{3a}$, $R_{3b}$, are hydrogen; $R_1$ is a 5- to 6-membered heteroaryl ring, cyanophenyl, a 8- to 12-membered bicyclic heteroaryl ring, or a 4- to 12-membered heterocyclic ring; and $R_4$ and $R_5$ taken together with the nitrogen atom to which they are attached form an amine moiety represented by structure:

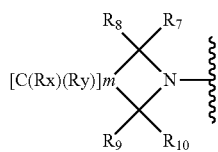

(II-a)

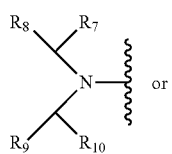

(II-b)

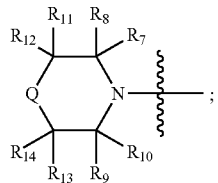

(II-c)

wherein $R_7$, $R_8$, $R_9$, and $R_{10}$ at each occurrence are independently selected from the group consisting of hydrogen, hydroxyalkyl, fluoroalkyl, cycloalkyl, and alkyl; $R_{11}$, $R_{12}$, $R_{13}$, and $R_{14}$ are each independently selected from the group consisting of hydrogen, hydroxyalkyl, alkyl, and fluoroalkyl; $R_x$ and $R_y$ are each independently selected from the group consisting of hydrogen, hydroxy, alkyl, alkoxy, alkylamino, fluoro, and dialkylamino; Q is O or S; and m is an integer from 1 to 5.

A. Chiral Resolution of Cyclopropanecarboxylic Acid with Chiral Amines

The process involves chiral resolution of an aryl-cyclopropanecarboxylic acid with a chiral amine. An illustration of this process step is shown below in Scheme 1:

Scheme 1

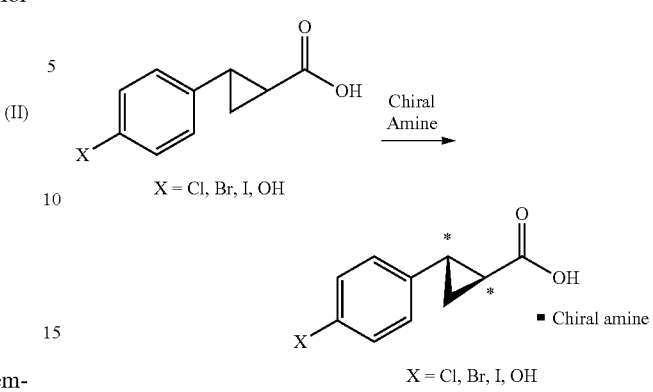

The cyclopropanecarboxylic acids:

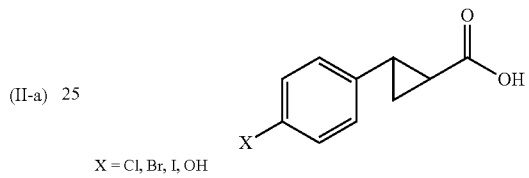

X = Cl, Br, I, OH is treated with a chiral amine to form a diasteromeric chiral salt, which can be further crystallized to form an enantiomerically pure salt. The enantiomerically pure arylcyclopropanecarboxylic acids salt can be broken-up to release the enantiomerically pure arylcyclopropanecarboxylic acids that can be further reacted with amines, reduced, and coupled with a suitable aromatic, heteroaromatic, or heterocycle group to provide compounds of formula (II). In one embodiment, the chiral amine is selected from the group consisting of (S)-(−)-α-methylbenzylamine, (R)-(+)-N-benzyl-α-methylbenzylamine, (S)-(−)-N-benzyl-α-methylbenzylamine, (R)-(+)-N,N-dimethyl-1-phenylethylamine, (S)-(−)-N,N-dimethyl-1-phenylethylamine, [R—(R*,R*)]-(+)-bis(a-methylbenzyl)amine, [S—(R*,R*)]-(−)-bis(a-methylbenzyl)amine, (S)-(+)-1-cyclohexylethylamine, (R)-(+)-1-(1-naphthyl)ethylamine, (S)-(−)-1-(1-naphthyl)ethylamine, (1R,2R,3R,5S)-(−)-isopinocamphenylamine, (1S,2S,3S,5R)-(+)-isopinocamphenylamine, (1R2R)-(−)-pseudoephedrine, (1S,2S)-(+)-pseudoephedrine, (1R,2S)-(−)-ephedrine, (1S,2R)-(+)-ephedrine, (1R,2S)-(−)-N-methylephedrine, (1S,2R)-(+)-N-methylephedrine, (1R,2S)-(−)-norephedrine, (1S,2R)-(+)-norephedrine, (1R,2S)-(+)-cis-1-amino-2-indanol, (1S,2R)-(−)-cis-1-amino-2-indanol, quinine, and cinchonine. In one embodiment, the chiral amine is (R)-(−)-1-cyclohexylethylamine. In another embodiment, the chiral amine is (R)-(+)-a-methylbenzylamine. In a preferred embodiment, the reaction is carried out in a polar organic solvent. In one embodiment the polar organic solvent is an alcohol. The alcohol can be selected from the group consisting of methanol, ethanol, isopropyl alcohol, tert-butyl alcohol, and n-butyl alcohol. In one embodiment, the alcohol is isopropyl alcohol. In another embodiment, the alcohol is tert-butyl alcohol. In one embodiment, the reaction is carried at a temperature of from about room temperature to about 75° C. In a particular embodiment, the temperature is from about 40° C. to about 60° C. In one particular embodiment, the temperature at which the reaction is carried out is from about 45° C. to about 50° C. Typically, the reaction is accomplished in a period of about 1 to 48 hours, however, the length of the reaction time can vary depending on the particular conditions and quality of the reagents, among other aspects of the reaction. In a preferred embodiment, the reaction is conducted for a time period of about 8 hours.

In another embodiment, the aryl-cyclopropanecarboxylic acid is prepared from arylaldehyde. An illustration of a process for preparing arylcyclopropanecarboxylic acid from aryl aldehyde is shown below in Scheme A.

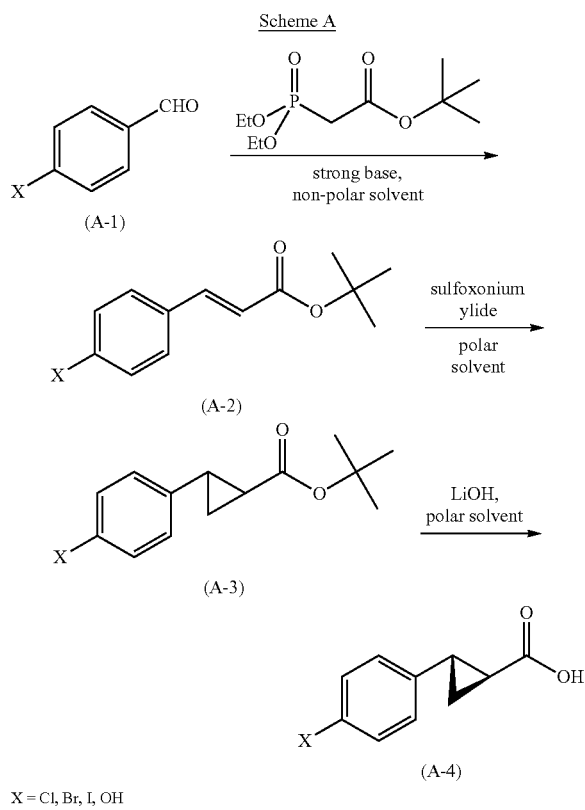

$X = Cl, Br, I, OH$

To prepare arylcyclopropanecarboxylic acid, aryl aldehyde (A-1) is treated with t-butyldimethylphosphonoacetate to provide tert-butyl arylacrylate (A-2). Tert-butyl arylacrylate is treated a sulfoxonium ylide to provide tert-butyl arylcyclopropanecarboxylic acid ester (A-3). Hydrolysis of the tert-butyl arylcyclopropanecarboxylic acid ester under basic conditions with lithium hydroxide provides arylcyclopropanecarboxylic acid (A-4).

In one embodiment, aryl aldehyde (A-1) is treated with t-butyldimethylphosphonoacetate with any strong base in a non-polar solvent. In one embodiment, the strong base is a metal hydride. Examples of metal hydride base are lithium hydride and sodium hydride. The strong base can also be potassium t-butyloxide, sodium t-butyloxide, lithium t-butyloxide. In one embodiment, sodium hydride (NaH) is the base or potassium t-butyloxide. The reaction is carried out in any non-polar solvent. The non-polar solvent is an organic solvent, for example, toluene, hexane, benzene, 1,4-dioxane, chloroform, or diethyl ether. In one embodiment, the organic solvent is toluene.

Suitable sulfoxonium ylides for treating tert-butyl arylacrylate (A-2) to provide tert-butyl arylcyclopropanecarboxylic acid ester (A-3) can be dimethylsulfoxonium iodide methylide (Corey-Chaykovsky Regent) and trimethylsulfoxonium iodide reagent. In one embodiment, the sulfoxonium reagent is trimethylsulfoxonium iodide reagent. In another embodiment, the sulfoxonium reagent is dimethylsulfoxonium iodide methylide. The reaction is carried out in a polar solvent. The polar solvent can be any suitable polar aprotic solvent. Examples of suitable polar aprotic solvents include, but are not limited to, dimethyl sulfoxide, dimethyl acetamide, dimethyl formamide, or mixtures thereof. In one particular embodiment, the solvent is a mixture of dimethyl sulfoxide and dimethyl acetamide. The mixture can be in a ratio of from about 1:1 to about 2:1 dimethyl sulfoxide/dimethyl acetamide. The reaction can be carried out at any temperature, however, in the reaction mixture is maintained at a temperature of less than about 10° C.

Any base is suitable for use in the hydrolysis of the ester of tert-butyl arylcyclopropanecarboxylic acid (A-3) to provide arylcyclopropanecarboxylic acid (A-4). In one embodiment, the base is any metal hydroxide base. Such base can include, for example, sodium hydroxide, lithium hydroxide, and potassium hydroxide.

B. Amide Formation

The enantiomerically pure arylcyclopropanecarboxylic acid:

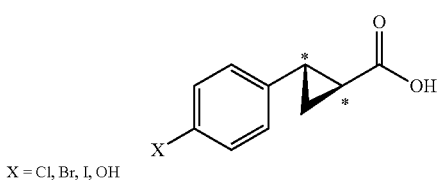

$X = Cl, Br, I, OH$ obtained from the chiral resolution is coupled with an amine. An illustration of the process is shown below in Scheme 2.

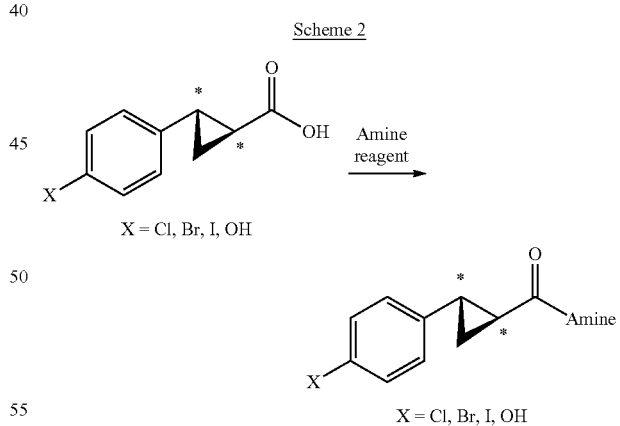

Suitable amine reagents can be represented by the formula:

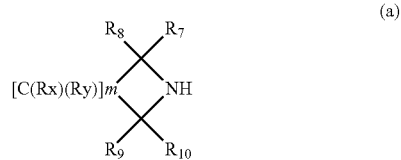

(a)

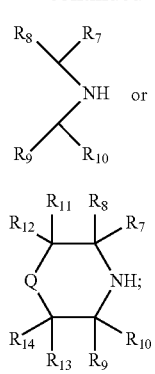

wherein $R_7$, $R_8$, $R_9$, and $R_{10}$ at each occurrence are independently selected from the group consisting of hydrogen, hydroxyalkyl, fluoroalkyl, cycloalkyl, and alkyl; $R_{11}$, $R_{12}$, $R_{13}$, and $R_{14}$ are each independently selected from the group consisting of hydrogen, hydroxyalkyl, alkyl, and fluoroalkyl; $R_x$ and $R_y$ are each independently selected from the group consisting of hydrogen, hydroxy, alkyl, alkoxy, alkylamino, fluoro, and dialkylamino; Q is O or S; and m is an integer from 1 to 5.

Suitable amines for the reaction can include any amine of formula (a), as defined above. Such amine can be more particularly selected from pyrrolidine, 2-(S)-methylpyrrolidine, 2-(R)-methylpyrrolidine, 3-methylpyrrolidine, 2-fluoropyrrolidine, 3-fluoropyrrolidine, 2-hydroxypyrrolidine, 3-hydroxypyrrolidine, 2-hydroxymethylpyrrolidine, and 3-hydroxymethylpyrrolidine. Other suitable amines can be more particularly selected from pyridine, 2-methylpyridine, 3-methylpyridine, 4-methylpyridine, 2-fluoropyridine, 3-fluoropyridine, 4-fluoropyridine, 2-hydroxypyridine, 3-hydroxypyridine, 4-hydroxymethylpyridine, 2-hydroxymethylpyridine, 3-hydroxymethylpyridine, and 4-hydroxymethylpyridine. In one particular embodiment, the amines are those wherein one of the substituents represented by $R_7$, $R_8$, $R_9$, and $R_{10}$ is hydrogen or alkyl and the other substituents are hydrogen. Particular preferred examples are pyrrolidine, 2-(S)-methylpyrrolidine, and 2-(R)-methylpyrrolidine.

Other suitable amines are those of formula (b), as defined above. Such amine may be more particularly selected from dimethylamine, diethylamine, methylamine, and ethylamine. In one particular embodiment, the amines are those wherein one of the substituents represented by $R_7$, $R_8$, $R_9$, and $R_{10}$ is hydrogen or alkyl and the other substituents are hydrogen. Particular preferred examples are dimethylamine and diethylamine.

Additional reagents having an amine group are those of formula (c), as defined above. Such amine may be more particularly selected from morpholine and thiomorpholine. In a particular embodiment, the amine reagent is morpholine.

The reaction is carried out using N,N'-carbonyldiimidazole. In a preferred embodiment, the arylcyclopropanecarboxylic acid, amine, and N,N'-carbonyldiimidazole are combined in an organic solvent. Examples of suitable organic solvents are tetrahydrofuran, toluene, 1,2-dimethoxyethane, 1,4-dioxane, N-methyl-pyrrolidinone, dimethylacetamide, and dimethylformamide. In one embodiment, the solvent is tetrahydrofuran. In another embodiment, the solvent is toluene. Tetrahydrofuran is the most preferred solvent. The reaction can be accomplished at room temperature. Typically, the reaction is accomplished in a period of about 1 to 48 hours, however, the length of the reaction time can vary depending on the particular conditions and quality of the reagents, among other aspects of the reaction. In a preferred embodiment, the reaction is conducted for a time period of about 8 hours.

C. Reduction of Amide

The resulting compound of formula:

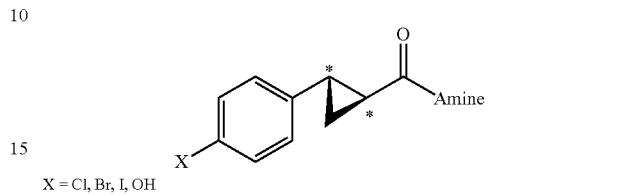

is reduced to provide a compound as shown below in Scheme 3.

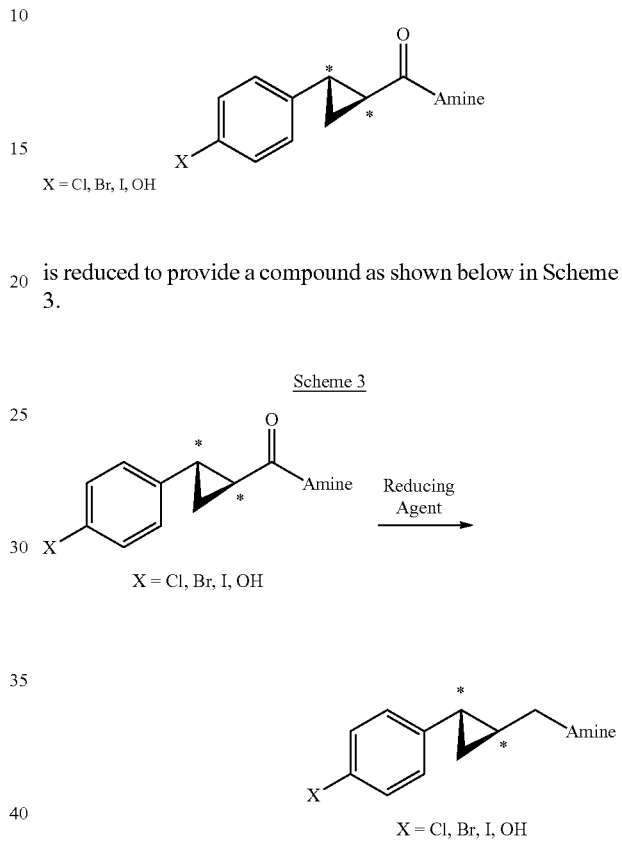

In one embodiment of the invention, the cyclopropanecarboxylic acid amide is reduced using a reducing agent selected from borane reducing reagents. Suitable reducing agents are, for example, borane tetrahydrofuran complex, diborane, borane dimethylsulfide complex, a combination of sodium borohydride and sodium trifluoride. In a preferred embodiment, the reaction is conducted in a polar, aprotic solvent. Examples of suitable solvents are tetrahydrofuran, 1,2-dimethoxyethane, 1,2-diethoxyethane, 2-methyltetrahydrofuran, 1,4-dioxane, and methyl-tert-butyl ethers. The preferred solvent is tetrahydrofuran. The reaction can be conducted at any suitable temperature. Typically, the reaction is conducted at a temperature between 0° C. and 80° C. In a preferred embodiment, the reaction is conducted at a temperature of about 50° C. Typically, the reaction is accomplished in a period of about 1 to 48 hours, however, the length of the reaction time can vary depending on the particular conditions and quality of the reagents, among other aspects of the reaction. In one embodiment, the reaction is conducted for a time period of about 8 hours.

D. Coupling with Aromatic, Heteroaromatic, and Heterocyclic Reagent

In one embodiment of the invention, the compound of formula:

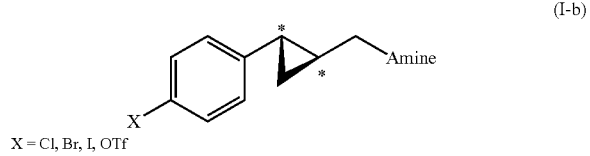

X = Cl, Br, I, OTf is reacted with a suitable aromatic or non-aromatic reagent to provide compounds of formula (II). An illustration of this process is shown below in Scheme 4.

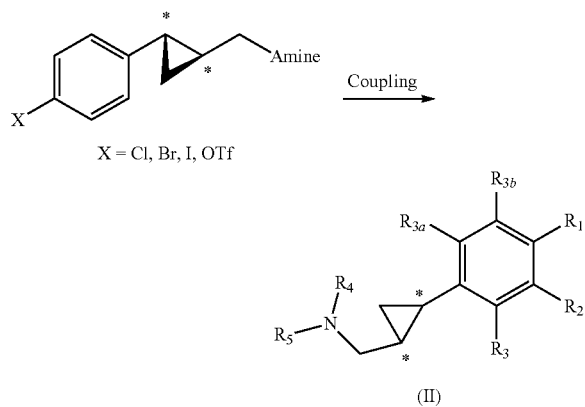

In a preferred embodiment, the compound of formula (I-b) undergoes coupling reactions to provide the compounds of formula (II). Coupling conditions, commonly referred to as metal-catalyzed reaction including palladium, nickel, iron or copper catalyzed reaction, such as Ullmann reaction conditions, are preferred for the reaction.

Any reagent suitable for providing a moiety within the definition of $R_1$ can be used. Reagents suitable for the reaction can include, for example, 5- to 6-membered heteroaryl, 8- to 12-membered bicyclic heteroaryl, and 4- to 12-membered heterocyclic reagents. Examples of particular 5- to 6-membered heteroaryl reagents include, but are not limited to, pyridazin-3(2H)-one, pyridin-2(1H)-one, pyrimidin-2(1H)-one, pyrimidin-2,4(1H,3H)-dione, pyrrolidin-2-one, benzo[d]thiazol-2(3H)-one, pyridin-4(1H)-one, pyrroline, imidazolidin-2-one, 1H-imidazol-2(3H)-one, piperidin-2-one, tetrahydropyrimidin-2(1H)-one, [1,2,4]thiadiazolone, [1,2,5]thiadiazolone, [1,3,4]thiadiazinone, [1,2,4]oxadiazolone, [1,2,5]oxadiazolone, and [1,3,4]oxadiazin-one. Examples of particular 4- to 12-membered heterocyclic reagents include, but are not limited to, azepane, azetidine, aziridine, azocane, dihydropyridine, dihydropyrimidine, piperidine, pyrrolidine, dihydrothiazole, dihydropyridine, thiomorpholine, dioxane, dithiane, tetrahydrofuran, dihydropyrane, tetrahydropyran, [1,3]dioxolane, azetidin-2-one, and azepan-2-one. Examples of particular 8- to 12-membered bicyclic heteroaryl reagents include, but are not limited to, isoindolin-1,3-dione, (Z)-1H-benzo[e][1,4]diazepin-5(4H)-one, and 1H-benzo[d]imidazol-2(3H)-one.

In one embodiment, the reaction is conducted with a copper catalyst and base in a polar aprotic solvent in the presence of N,N'-dimethylenediamine. The copper catalyst can be any copper catalyst. In a preferred embodiment, the copper catalyst is a copper (I) catalyst. Examples of such catalysts are, for example, copper (I) iodide, copper (I) bromide, and copper (I) chloride. Copper (I) iodide is preferred.

The base is any suitable organic base. Examples of such base can include, for example, potassium carbonate ($K_2CO_3$), potassium phosphate ($K_3PO_4$), cesium carbonate ($Cs_2CO_3$), sodium methoxide (NaOMe), sodium tert-butoxide (NaOt-Bu), sodium acetate (NaOAc), and potassium tert-butoxide (KOt-Bu). In one embodiment, the base is $K_2CO_3$. In another embodiment, the base is $K_3PO_4$.

The basic solvent can be any polar aprotic solvent. Examples of such solvents are, for example, dimethyl acetamide, dimethyl formamide, 1-methyl-2-pyrrolidinone, and pyridine. In a preferred embodiment the polar aprotic solvent is pyridine.

The reaction can be conducted at any suitable temperature. Typically, the reaction is conducted at a temperature between 0° C. and 140° C. In a preferred embodiment, the reaction is conducted at a temperature of about 115° C. Typically, the reaction is accomplished in a period of about 1 to 48 hours, however, the length of the reaction time can vary depending on the particular conditions and quality of the reagents, among other aspects of the reaction. In one embodiment, the reaction is conducted for a time period of about 8 hours.

E. Intermediates

In addition to the processes described above, certain intermediates prepared during the processes are new and useful for preparing enantiomerically pure cyclopropyl amine derivatives as described. Accordingly, the present invention, in one embodiment, also relates to compounds that are:

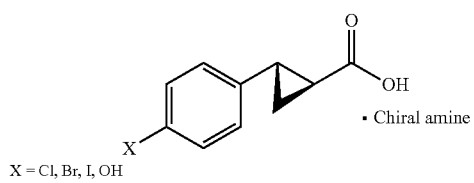

X = Cl, Br, I, OH wherein, the chiral amines are (S)-(−)-α-methylbenzylamine, (R)-(+)-N-benzyl-a-methylbenzylamine, (S)-(−)-N-benzyl-α-methylbenzylamine, (R)-(+)-N,N-dimethyl-1-phenylethylamine, (S)-(−)-N,N-dimethyl-1-phenylethylamine, [R—(R*,R*)]-(+)-bis(α-methylbenzyl)amine, [S-(R*,R*)]-(−)-bis(a-methylbenzyl)amine, (S)-(+)-1-cyclohexylethylamine, (R)-(+)-1-(1-naphthyl)ethylamine, (S)-(−)-1-(1-naphthyl)ethylamine, (1R,2R,3R,5S)-(−)-isopinocamphenylamine, (1S,2S,3S,5R)-(+)-isopinocamphenylamine, (1R2R)-(−)-pseudoephedrine, (1S,2S)-(+)-pseudoephedrine, (1R,2S)-(−)-ephedrine, (1S,2R)-(+)-ephedrine, (1R,2S)-(−)-N-methylephedrine, (1S,2R)-(+)-N-methylephedrine, (1R,2S)-(−)-norephedrine, (1S,2R)-(+)-norephedrine, (1R,2S)-(+)-cis-1-amino-2-indanol, (1S,2R)-(−)-cis-1-amino-2-indanol, quinine, or cinchonine. The chiral amines also can be selected from (R)-(−)-1-cyclohexylethylamine or (R)-(+)-α-methylbenzylamine. In one embodiment, the chiral amine is (R)-(−)-1-cyclohexylethylamine. In another embodiment, the chiral amine is (R)-(+)-α-methylbenzylamine.

In another embodiment, the present invention also relates to compounds that are:

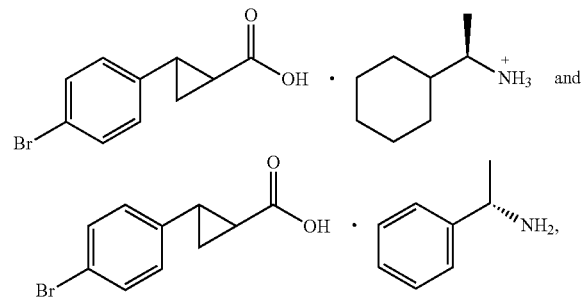

i.e. 2-(4-bromophenyl)cyclopropanecarboxylic acid R-(−)-1-cyclohexylethylamine salt and 2-(4-bromophenyl)cyclopropanecarboxylic acid (R)-(+)-α-methylbenzylamine salt.

In addition, the present invention, in another embodiment, relates to a compound of formula:

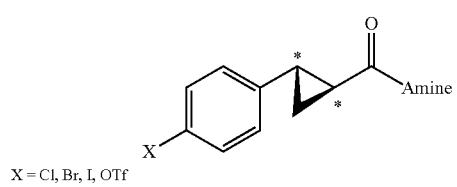

X = Cl, Br, I, OTf wherein the amine moiety in the structure above is represented by:

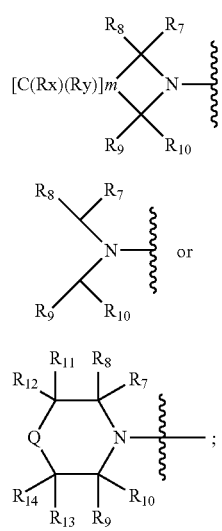

wherein $R_7$, $R_8$, $R_9$, and $R_{10}$ at each occurrence are independently selected from the group consisting of hydrogen, hydroxyalkyl, fluoroalkyl, cycloalkyl, and alkyl; $R_{11}$, $R_{12}$, $R_{13}$, and $R_{14}$ are each independently selected from the group consisting of hydrogen, hydroxyalkyl, alkyl, and fluoroalkyl; $R_x$ and $R_y$ are each independently selected from the group consisting of hydrogen, hydroxy, alkyl, alkoxy, alkylamino, fluoro, and dialkylamino; Q is O or S; and m is an integer from 1 to 5.

Still yet, the present invention, in another embodiment, relates to a compound of formula:

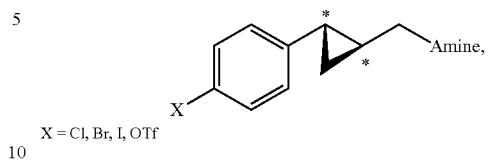

X = Cl, Br, I, OTf wherein the amine moiety in the structure above is represented by:

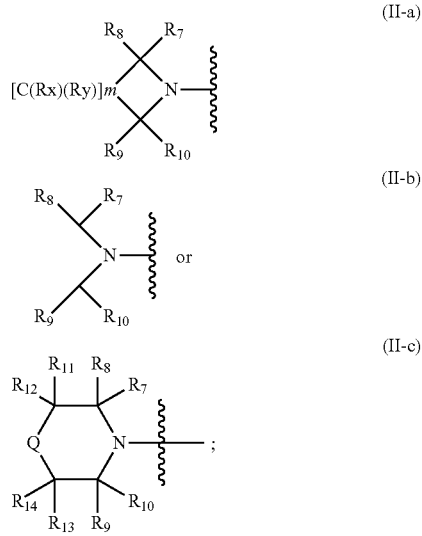

wherein $R_7$, $R_8$, $R_9$, and $R_{10}$ at each occurrence are independently selected from the group consisting of hydrogen, hydroxyalkyl, fluoroalkyl, cycloalkyl, and alkyl; $R_{11}$, $R_{12}$, $R_{13}$, and $R_{14}$ are each independently selected from the group consisting of hydrogen, hydroxyalkyl, alkyl, and fluoroalkyl; $R_x$ and $R_y$ are each independently selected from the group consisting of hydrogen, hydroxy, alkyl, alkoxy, alkylamino, fluoro, and dialkylamino; Q is O or S; and m is an integer from 1 to 5.

F. Isotopically-Labeled Compounds

The present invention also includes isotopically-labeled compounds, which are identical to those recited in Formula (I-a), (I-b), and (II), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, fluorine, and chlorine, such as but not limited to $^2H$, $^3H$, $^{13}C$, $^{15}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art using appropriate isotopically-labeled reagent in place of non-isotopically-labeled reagent.

G. Compositions

The cyclopropyl amine derivatives of formula (II) and salts prepared by the above processes can be used to prepare compositions. These compositions typically also comprise one or more conventional pharmaceutically acceptable carriers, adjuvants, and/or vehicles (together referred to as "excipients").

Compositions for oral administration, and solid dosage forms in particular, are preferred. Such solid dosage forms include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

H. Methods of Use

The compounds and compositions of the invention are useful for treating and preventing certain diseases and disorders in humans and animals. As an important consequence of the ability of the compounds of the invention to modulate the effects of histamine-3 receptors in cells, the compounds described in the invention can affect physiological processes in humans and animals. In this way, the compounds and compositions described in the invention are useful for treating and preventing diseases and disorders modulated by histamine-3 receptors. Typically, treatment or prevention of such diseases and disorders can be effected by selectively modulating the histamine-3 receptors in a mammal, by administering a compound or composition of the invention, either alone or in combination with another active agent as part of a therapeutic regimen.

The compounds of the invention, including but not limited to those specified in the examples, possess an affinity for the histamine-3 receptors and therefore, the compounds of the invention may be useful for the treatment and prevention of diseases or conditions such as attention-deficit hyperactivity disorder (ADHD), deficits in attention, dementia, and diseases with deficits of memory, learning, schizophrenia, cognitive deficits of schizophrenia, cognitive deficits and dysfunction in psychiatric disorders, Alzheimer's disease, mild cognitive impairment, epilepsy, seizures, allergic rhinitis, and asthma, motion sickness, dizziness, Meniere's disease, vestibular disorders, vertigo, obesity, diabetes, type II diabetes, Syndrome X, insulin resistance syndrome, metabolic syndrome, pain, including neuropathic pain, neuropathy, sleep disorders, narcolepsy, pathological sleepiness, jet lag, drug abuse, mood alteration, bipolar disorder, depression, obsessive compulsive disorder, Tourette's syndrome, Parkinson's disease, and medullary thyroid carcinoma, melanoma, and polycystic ovary syndrome.

The preferred total daily dose of a compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the severity of the pathological condition; pharmacological considerations, such as the activity, efficacy, pharmacokinetic, and toxicology profiles of the particular compound or salt used; whether a drug delivery system is utilized; and the specific drug combination. Thus, the dosage regimen actually employed can vary widely, and therefore, can derive from the preferred dosage regimen set forth above.

EXAMPLES

The present invention is illustrated by the following examples. It will be understood, however, that the invention is not limited to the specific details of the examples. It will be clear to one with skill in the art that the processes of invention, as described by the Schemes, Detailed Description, and Examples provided herein, would be suitable for preparing the other enantiomer of any of the compounds and intermediates described by the Schemes or the Examples, with the resulting compound having the opposite stereochemistry as described.

Example 1

Preparation of 2-(4-bromophenyl)cyclopropanecarboxylic acid (4)

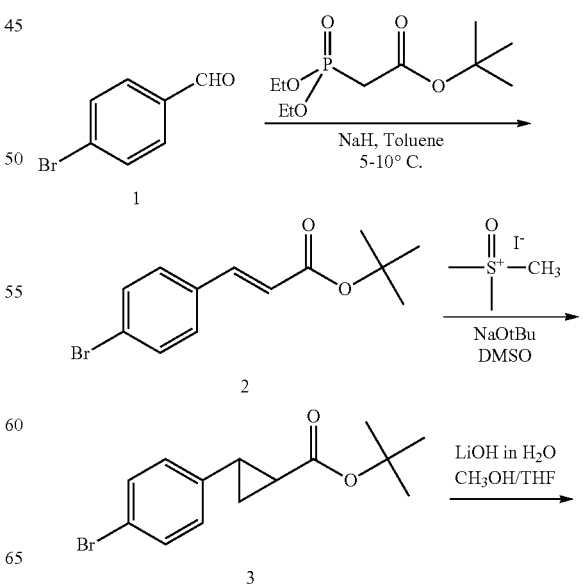

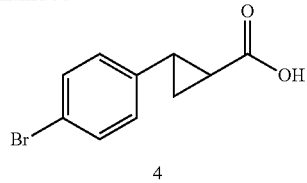

4

Example 1a

Preparation of (E)-tert-butyl 3-(4-bromophenyl)acrylate (2)

To a three-necked flask was charged with NaH (95%, 2.6 g, 103 mmol) followed by Toluene (250 ml). The suspension was cooled to 5° C. and to the mixture was added the t-butyldimethylphosphonoacetate (95%, 25.5 ml, 103 mmol) slowly keeping the temperature below 5° C. (very little exotherm observed and $H_2$ gas generated), the resulting mixture was stirred at 5° C. for NLT 20 min until no more $H_2$ gas was generated). To the above mixture was then added the aldehyde (17.6 g, 94.2 mmol) and the resulting mixture was stirred at 10° C. for 2 hours and then at room temperature overnight. The reaction was monitored by HPLC until the starting material is consumed (<1.0 pa % of aldehyde). The reaction mixture was poured into 400 ml of water and the organic layer was separated and washed with brine (400 ml), dried with $Na_2SO_4$ and concentrated to give an oil, which solidified upon standing to give crude product which was purified by crystallization from ethanol/water water (1:1, 30 mL/g) to give 25 g of product. $^1$H NMR (400 MHz, DMSO-$d_6$) δ 1.47 (s, 9H), 6.53 (d, 1H, J=15.92), 7.50 (d, 1H, J=16.05), 7.57 (d, 2H, J=8.51), 7.63 (d, 2H, J=8.51). $^{13}$C NMR (100 MHz, DMSO-$d_6$) δ 27.8, 79.8, 120.3, 123.0, 129.6, 131.3, 132.9, 141.6 & 164.6 with 4 peaks overlapping. A sample of the isolated product was purified by crystallization from ethanol/water (1:1, 30 mL/g). $^1$H NMR (400 MHz, DMSO-$d_6$) δ 1.47 (s, 9H), 6.53 (d, 1H, J=15.92), 7.50 (d, 1H, J=16.05), 7.57 (d, 2H, J=8.51), 7.63 (d, 2H, J=8.51). $^{13}$C NMR (100 MHz, DMSO-$d_6$) δ 27.8, 79.8, 120.3, 123.0, 129.6, 131.3, 132.9, 141.6 & 164.6 with 4 peaks overlapping.

Example 1b

Preparation of tert-butyl 2-(4-bromophenyl)cyclopropanecarboxylate (3)

In a round-bottom flask, mixed trimethylsulfoxonium iodide (6.6 g, 30 mmol) in dimethyl sulfoxide (28 mL, KF=266 ppm $H_2O$) and dimethylacetamide (12 mL, KF=249 ppm $H_2O$). Added sodium tert-butoxide (2.7 g, 28 mmol) in one portion. Stirred the suspension for NLT 0.5 H at room temperature. Separately, mixed (E)-tert-butyl 3-(4-bromophenyl)acrylate 1 (5.66 g, 20 mmol) in dimethyl sulfoxide (20 mL) and heated to 50° C. Then, transferred the sulfur ylide mixture (slight suspension) by cannula (<10 min addition). The flask/cannula were rinsed into the reaction mixture with dimethyl sulfoxide (2-4 mL). Stirred the resulting yellow solution at 50° C., monitoring by HPLC for reaction completion (<1% pA of 1 after 0.5 h). Cooled the reaction mixture to <10° C. before quenching (exothermic) by slow addition with water (120 mL, product precipitates). The resulting product slurry was stirred at room temperature (1-2 h) and then filtered. The flask and wetcake were washed with water (~70 mL total). The wetcake was dried under vacuum at 45° C. Isolated 4.44 g of an off-white solid (98% pA, 96 wt %) in 71% wt-adjusted yield. A sample of the isolated product was further purified by crystallization from methanol/water (1:1, 20 mL/g). $^1$H NMR (400 MHz, CDCl$_3$) δ 1.16-1.21 (m, 1H), 1.47 (s, 9H), 1.50-1.55 (m, 1H), 1.77-1.81 (m, 1H), 2.37-2.41 (m, 1H), 6.95 (d, 2H, J=8.37), 7.37 (d, 2H, J=8.51). $^{13}$C NMR (100 MHz, CDCl$_3$) δ 17.3, 25.4, 25.5, 28.4, 80.7, 119.7, 127.5, 131.1, 139.2, 171.7 with 4 peaks overlapping.

Example 1c

Preparation of 2-(4-bromophenyl)cyclopropanecarboxylic acid (4)

In a round bottom flask, mixed the tert-butyl 2-(4-bromophenyl)cyclopropanecarboxylate 2 (3.7 g, 12.0 mmol) in methanol/tetrahydrofuran (1:1, 30 mL) and heated to 50° C. Separately dissolved lithium hydroxide (1.4 g, 60 mmol) in water (15 mL) and then added to the solution of 2. Increased the heat to 65° C., and monitored by HPLC for reaction completion (<1% pA of 2, ~3 h). The reaction mixture was then cooled to room temperature and distilled to ½ volume. Cooled the suspension to <20° C. and acidified (exothermic addition) the product mixture to pH<2 with 2N HCl (~30 mL) to precipitate the product. Stirred the resulting suspension at 20° C. for NLT 0.5 h. Filtered the suspension and washed the wetcake with water (~20 mL). Dried the wetcake at 45° C. under vacuum. Isolated 2.96 g of an off-white solid (98% pA, 97 wt %=99% wt-adjusted yield). $^1$H NMR (400 MHz, CDCl$_3$) δ 1.35-1.40 (m, 1H), 1.65-1.69 (m, 1H), 1.85-1.89 (m, 1H), 2.53-2.58 (m, 1H), 6.97 (d, 2H, J=8.37), 7.40 (d, 2H, J=8.37). $^{13}$C NMR (100 MHz, CDCl$_3$) δ 17.7, 24.2, 26.7, 120.2, 127.7, 131.3, 138.1 & 178.9 with 2 peaks overlapping.

Example 2

Preparation of 2-(4-bromophenyl)cyclopropanecarboxylic acid, R-(−)-1-cyclohexylethylamine salt

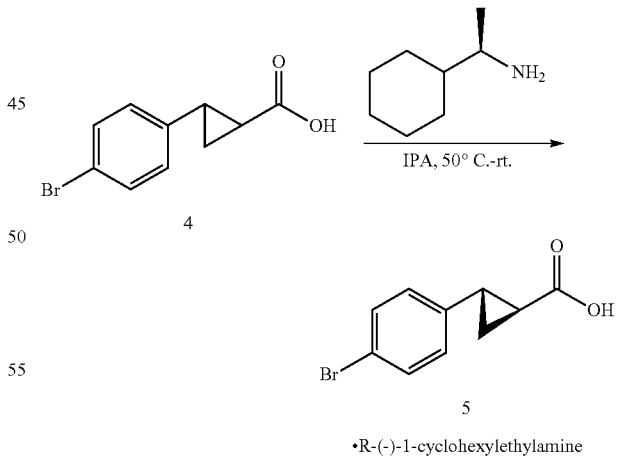

Example 2

Preparation of 2-(4-bromophenyl)cyclopropanecarboxylic acid, R-(−)-1-cyclohexylethylamine salt. (5)

In a round-bottom flask, mixed the racemic 2-(4-bromophenyl)cyclopropanecarboxylic acid (2.0 g, 8.3 mmol) in isopropyl alcohol (37 mL, 20 mL/g total volume) and heated to 50° C. Added a solution of the R-(−)-1-cyclohexylethylamine (1.1 g, 8.3 mmol) in isopropyl alcohol (3 mL). In <5 min a suspension formed. Continued to stir the suspension at 50° C. for 2 h. Then slowly cooled to room temperature (1-2 h) and stirred the suspension overnight (~15 h). The suspension was filtered. The flask and wetcake were rinsed with the mother liquors, followed by isopropyl alcohol (5 mL). The wetcake was dried on the filter under vacuum (1.88 g, 61.5% ee). The wetcake was then charged back to the round-bottom flask with isopropyl alcohol (38 mL, 20 mL/g). The suspension was heated to 80° C. After 0.5 h, all solids dissolved. The solution was then slowly cooled to 50° C. (~2 h), during which time a suspension formed. The suspension was stirred at 50° C. for 2 h, and then slowly cooled to room temperature (1-2 h). Stirred the suspension overnight (~15 h) at room temperature. The suspension was filtered. The flask and wetcake were rinsed with the liquors, followed by isopropyl alcohol (5 mL). The wetcake was dried under vacuum at 45° C. Isolated 1.25 g (97.8% ee, ~81% recovery). $^1$H NMR (400 MHz, CD$_3$OD) δ 0.98-1.12 (m, 3H), 1.12-1.21 (m, 1H), 1.23 (d, 3H, J=6.72), 1.24-1.36 (m, 2H), 1.39-1.45 (m, 1H), 1.45-1.55 (m, 1H), 1.65-1.86 (m, 6H), 2.25-2.32 (m, 1H), 3.00-3.08 (m, 1H), 7.00 (d, 2H, J=8.37), 7.35 (d, 2H, J=8.51). $^{13}$C NMR (100 MHz, CD$_3$OD) δ 16.2, 17.2, 25.3, 27.1, 27.1, 27.2, 28.9, 29.0, 30.1, 42.8, 53.3, 119.7, 128.4, 131.8, 142.4, 180.4 with 2 peaks overlapping.

Example 3

Preparation of 2-(4-((1S,2S)-2-(((S)-2-methylpyrrolidin-1-yl)methyl)cyclopropyl)phenyl)pyridazin-3(2H)-one, L-tartrate monohydrate salt

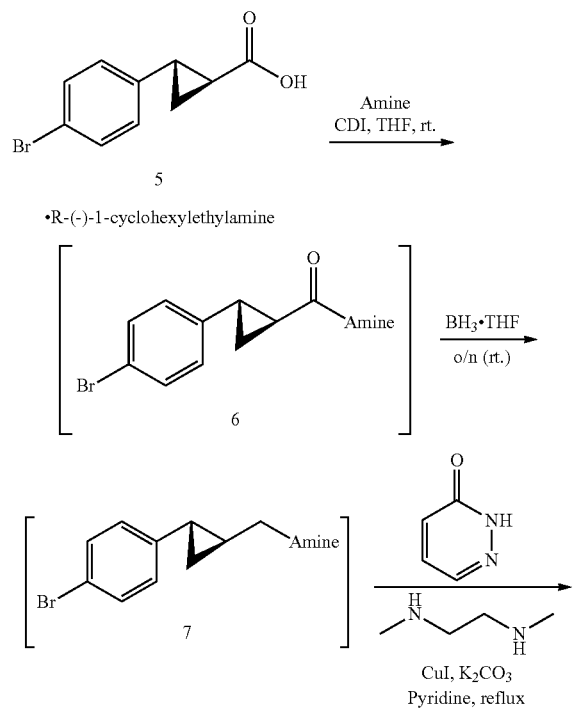

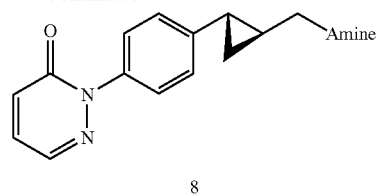

8

L-tartrate salt monohydrate

Example 3a

Preparation of a Compound of Structure 6, Scheme 3

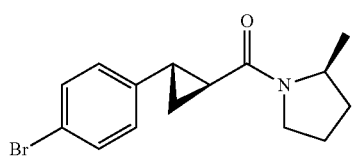

6a ((1S,2S)-2-(4-bromophenyl)cyclopropyl)(amino)methanone (6a)

The chiral salt 5 was first broken up by treating it with citric acid solution, exacted with MTBE and drying to obtain the free acid, 2-(4-bromophenyl)cyclopropanecarboxylic acid 4 (4.82 g, 20 mmol) and mixed with 1,1'-carbonyldiimidazole (4.22 g, 26 mmol) in THF (45 mL, 10 mL/g total volume). A suspension formed after stirring at room temperature for >30 min. The suspension was cooled to ~15° C. Then a solution of the (S)-2-methylpyrrolidine (2.55 g, 30 mmol) in THF (5 mL) was added over ~5 min. The mixture was stirred at room temperature and monitored by HPLC for reaction completion (typically <1 h). Tert-butyl methyl ether (60 mL) was added and the resulting mixture was extracted with a 10% solution of citric acid (40 mL, 4×), followed by a water wash (40 mL). The organic product layer was then concentrated to ~¼ volume (3-4 mL/g) and then chased with THF (50 mL, 2×). The product solution in THF was then diluted with more THF to ~10 mL/g and assayed by HPLC against a known standard. 6.1 g product was assayed (99% assayed yield, 98% peak area). A sample was purified by silica gel chromatography and then concentrated in vacuo under high vacuum to an oil that crystallized at room temperature to provide the standard. $^1$H NMR (400 MHz, DMSO-d$_6$) δ 0.97/1.08 (d, 3H, J=6.4), 1.14-1.19 (m, 1H), 1.38-1.43/1.46-1.51 (m, 1H), 1.46-1.51/1.56-1.63 (m, 1H), 1.72-2.08 (m, 4H), 2.16-2.26 (m, 1H), 3.24-3.30/3.33-3.43 (m, 1H), 3.33-3.43/3.62-3.67 (m, 1H), 3.97-4.04/4.18-4.25 (m, 1H), 7.12/7.13 (d, 2H, J=8.4), 7.41/7.43 (d, 2H, J=8.4). $^{13}$C NMR (100 MHz, DMSO-d$_6$) δ 15.9/16.2, 19.5/21.7, 21.7/23.4, 24.1/24.3, 24.6/24.7, 31.4/32.7, 45.6/46.4, 52.1/52.2, 118.3/118.4, 127.5/127.7, 130.5/130.6, 140.0/140.1, 167.8/167.9 with 2 peaks overlapping.

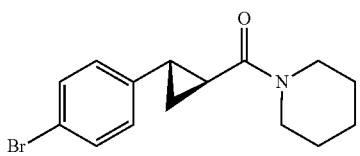

(((1S,2S)-2-(4-bromophenyl)cyclopropyl)(piperidin-1-yl)methanone (6b)

Following the general procedure, reaction of 5 (3.62 g, 15 mmol) with CDI (3.16 g, 19.5 mmol) and piperidine (2.22 mL, 22.5 mmol) afforded 6b in an assay yield of 4.55 g (14.8 mmol, 99% assay yield, 99% peak area). A sample was purified by washing the product solution with 5% NaHCO₃ and concentrating in vacuo to an oil that solidified at room temperature to provide the standard.

$^1$H NMR (400 MHz, DMSO) δ 7.43 (d, J=8.5, 2H), 7.14 (d, J=8.5, 2H), 3.74-3.53 (m, 2H), 3.44 (s, 2H), 2.32-2.16 (m, 2H), 1.69-1.50 (m, 2H), 1.50-1.33 (m, 5H), 1.16 (ddd, J=8.1, 6.3, 3.9, 1H). $^{13}$C NMR (101 MHz, DMSO) δ 168.08, 140.12, 130.53, 127.69, 118.31, 45.86, 42.57, 26.35, 25.30, 24.21, 23.85, 22.57, 16.29. MS (ESI+) 308, 310 (M+H).

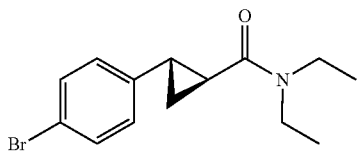

(1S,2S)-2-(4-bromophenyl)-N,N-diethylcyclopropanecarboxamide (6c)

Following the general procedure, reaction of 5 (3.62 g, 15 mmol) with CDI (3.16 g, 19.5 mmol) and diethylamine (2.33 mL, 22.5 mmol) afforded 6c in an assay yield of 4.18 g (14.1 mmol, 94% assay yield, 98% peak area). A sample was purified by washing the product solution with 5% NaHCO₃ and concentrating in vacuo to an oil to provide the standard.

$^1$H NMR (400 MHz, DMSO) δ 7.43 (d, J=8.5, 2H), 7.14 (d, J=8.5, 2H), 3.50 (dq, J=14.2, 7.1, 1H), 3.41-3.29 (m, 2H), 3.24 (dq, J=14.0, 7.1, 1H), 2.25 (ddd, J=8.9, 6.1, 4.3, 1H), 2.15 (ddd, J=8.3, 5.3, 4.3, 1H), 1.41 (ddd, J=9.0, 5.3, 3.9, 1H), 1.18 (ddd, J=8.3, 6.1, 3.8, 1H), 1.06 (t, J=7.1, 3H), 1.01 (t, J=7.1, 3H). $^{13}$C NMR (101 MHz, DMSO) δ 168.82, 140.08, 130.54, 127.64, 118.32, 41.44, 40.17, 24.23, 22.82, 16.43, 15.01, 13.34. MS (ESI+) 296, 298 (M+H).

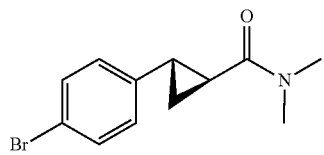

(1S,2S)-2-(4-bromophenyl)-N,N-dimethylcyclopropanecarboxamide (6d)

Following the general procedure, reaction of 5 (3.62 g, 15 mmol) with CDI (3.16 g, 19.5 mmol) and 2 M dimethylamine in THF (11.25 mL, 22.5 mmol) afforded 6d in an assay yield of 3.67 g (13.7 mmol, 91% assay yield, 99% peak area). A sample was purified by washing the product solution with 5% NaHCO₃ and concentrating in vacuo to an oil that solidified at room temperature to provide the standard.

$^1$H NMR (400 MHz, DMSO) δ 7.43 (d, J=8.5, 2H), 7.14 (d, J=8.5, 2H), 3.07 (s, 3H), 2.84 (s, 3H), 2.30-2.18 (m, 2H), 1.42-1.33 (m, 1H), 1.19 (ddd, J=8.3, 6.2, 3.9, 1H). $^{13}$C NMR (101 MHz, DMSO) δ 169.68, 140.05, 130.52, 127.71, 118.32, 36.72, 35.20, 24.09, 22.59, 16.45. MS (ESI+) 268, 270 (M+H).

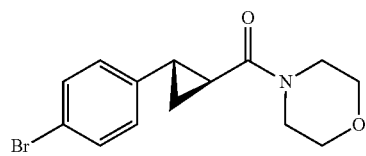

(((1S,2S)-2-(4-bromophenyl)cyclopropyl)(morpholino)methanone (6e)

Following the general procedure, reaction of 5 (3.62 g, 15 mmol) with CDI (3.16 g, 19.5 mmol) and morpholine (1.96 mL, 22.5 mmol) afforded 6e in an assay yield of 4.48 g (14.45 mmol, 96% assay yield, 100% peak area). A sample was purified by washing the product solution with 5% NaHCO₃ and concentrating in vacuo to a white solid to provide the standard.

$^1$H NMR (400 MHz, CDCL₃) δ 7.42 (d, J=8.4, 2H), 7.00 (d, J=8.4, 2H), 3.82-3.54 (m, 8H), 2.50 (ddd, J=9.1, 6.2, 4.2, 1H), 1.93 (ddd, J=8.3, 5.3, 4.3, 1H), 1.77-1.65 (m, 1H), 1.30 (ddd, J=8.3, 6.2, 4.5, 1H). $^{13}$C NMR (101 MHz, CDCL₃) δ 169.72, 139.43, 131.19, 127.42, 119.68, 66.82, 66.73, 46.11, 25.20, 23.27, 16.53. MS (DCI+) 310, 312 (M+H), 327, 329 (M+NH4).

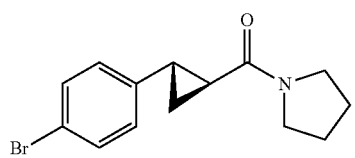

(((1S,2S)-2-(4-bromophenyl)cyclopropyl)(pyrrolidin-1-yl)methanone (6f)

Following the general procedure, reaction of 5 (3.62 g, 15 mmol) with CDI (3.16 g, 19.5 mmol) and pyrrolidine (1.86 mL, 22.5 mmol) afforded 6f in an assay yield of 4.24 g (14.40 mmol, 96% assay yield, 100% peak area). A sample was purified by washing the product solution with 5% NaHCO₃ and concentrating in vacuo to a white solid to provide the standard.

$^1$H NMR (400 MHz, CDCL₃) δ 7.41 (d, J=8.5, 2H), 7.01 (d, J=8.4, 2H), 3.72-3.47 (m, 4H), 2.51 (ddd, J=9.0, 6.2, 4.2, 1H), 2.09-1.82 (m, 5H), 1.69 (ddd, J=9.1, 5.3, 4.3, 1H), 1.32-1.19 (m, 1H). $^{13}$C NMR (101 MHz, CDCl$_3$) δ 169.47, 139.94, 131.07, 127.51, 119.45, 46.21, 26.25, 24.97, 24.67, 16.59. MS (DCI+) 294, 296 (M+H), 311, 313 (M+NH4).

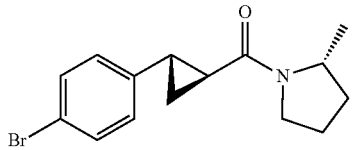

(((1S,2S)-2-(4-bromophenyl)cyclopropyl)((R)-2-methylpyrrolidin-1-yl)methanone (6 g)

Following the general procedure, reaction of 5 (3.62 g, 15 mmol) with CDI (3.16 g, 19.5 mmol) and (R)-2-methylpyrrolidine (1.92 g, 22.5 mmol) afforded 6 g in an assay yield of 4.62 g (15.00 mmol, 100% assay yield, 97.5% peak area). A sample was purified by washing the product solution with 5% NaHCO$_3$ and concentrating in vacuo to an oil that solidified at room temperature to provide the standard.

$^1$H NMR (400 MHz, CDCL$_3$) δ 7.43-7.38 (m, 2H), 7.04-6.97 (m, 2H), 4.30-4.06 (m, 1H), 3.70-3.43 (m, 2H), 2.54 (dddd, J=19.1, 9.1, 6.2, 4.2, 1H), 2.18-1.81 (m, 4H), 1.75-1.54 (m, 2H), 1.32-1.26 (m, 2H), 1.26-1.18 (m, 2H). $^{13}$C NMR (101 MHz, CDCL$_3$) δ 169.31, 169.22, 140.07, 139.94, 131.08, 131.04, 127.57, 127.50, 119.46, 119.40, 53.26, 53.14, 47.09, 46.14, 33.39, 32.16, 25.08, 24.95, 24.92, 24.83, 24.08, 22.29, 21.94, 19.97, 16.95, 16.78. MS (DCI+) 308, 310 (M+H), 325, 327 (M+NH4).

Example 3b

Preparation of a Compound of Structure 7, Scheme 3

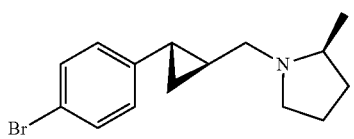

(S)-1-(((1S,2S)-2-(4-bromophenyl)cyclopropyl)methyl)-amine (7a)

The solution of the amide 6a (3.0 g assayed, 9.8 mmol) in THF (KF=561 ppm H$_2$O) was stirred at room temperature under N$_2$. A 1M solution of Borane-THF complex (34.2 mL) was added and the reaction mixture was stirred at room temperature. The reaction mixture was monitored by HPLC for reaction completion (typically >16 h). Upon completion (<1% starting material), the reaction is quenched with slow addition of 2N HCl (20 mL) to control the evolving gas. The product solution is then heated to 65° C. The product solution is monitored by HPLC until the boron-complexed product is completely broken (typically >10 h). The product solution is then cooled to room temperature and extracted with t-butyl methyl ether (40 mL, 2×). The aqueous product solution is then basified to pH=10 with 10% solution of sodium hydroxide in the presence of MTBE (40 mL). The basic aqueous layer is then extracted with more MTBE (40 mL). The organic layers are combined and washed with saturated sodium chloride solution (40 mL). The resulting product solution was assayed by HPLC against a known standard. 2.66 g product was assayed (92% assayed yield, >99% peak area). A sample was concentrated under high vacuum to an oil to provide a standard. $^1$H NMR (400 MHz, CDCl$_3$) δ 0.82-0.87 (m, 1H), 0.88-0.93 (m, 1H), 1.10 (d, 3H, J=6.03), 1.18-1.26 (m, 1H), 1.36-1.46 (m, 1H), 1.60-1.70 (m, 2H), 1.72-1.80 (m, 1H), 1.82-1.94 (m, 2H), 2.10-2.16 (m, 1H), 2.18-2.27 (m, 1H), 2.99-3.03 (m, 1H), 3.20-3.24 (m, 1H), 6.89 (d, 2H, J=8.37), 7.32 (d, 2H, J=8.51). $^{13}$C NMR (100 MHz, CDCl$_3$) δ 14.7, 19.3, 21.9, 23.0, 23.5, 32.7, 54.6, 58.3, 59.9, 118.6, 127.0, 130.9, 141.7 with 2 peaks overlapping.

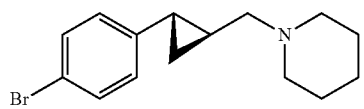

1-(((1S,2S)-2-(4-bromophenyl)cyclopropyl)methyl)piperidine (7b)

Following the general procedure, reaction of 6b (3.70 g assayed, 12.0 mmol) with 1 M BH$_3$ in THF (42.0 mL, 42.0 mmol) afforded 7b in an assay yield of 2.77 g (9.4 mmol, 78% assay yield, 99% peak area). A sample was concentrated in vacuo to an oil to provide the standard.

$^1$H NMR (400 MHz, CDCL$_3$) δ 7.38 (d, J=8.3, 2H), 6.94 (d, J=8.4, 2H), 2.57-2.41 (m, 5H), 2.34 (dd, J=12.7, 6.8, 1H), 1.69-1.58 (m, 5H), 1.51-1.42 (m, 2H), 1.30-1.20 (m, 1H), 0.95 (dt, J=8.6, 5.1, 1H), 0.87 (dt, J=8.6, 5.4, 1H). $^{13}$C NMR (101 MHz, CDCL$_3$) δ 141.77, 130.93, 127.08, 118.61, 63.77, 54.57, 26.21, 24.62, 22.63, 21.34, 15.71. MS (ESI+) 294, 296 (M+H).

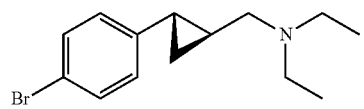

N-(((1S,2S)-2-(4-bromophenyl)cyclopropyl)methyl)-N-ethylethanamine (7c)

Following the general procedure, reaction of 6c (3.55 g assayed, 12.0 mmol) with 1 M BH$_3$ in THF (42.0 mL, 42.0 mmol) afforded 7c in an assay yield of 2.98 g (10.6 mmol, 88% assay yield, 99% peak area). A sample was concentrated in vacuo to an oil to provide the standard.

$^1$H NMR (400 MHz, CDCL$_3$) δ 7.38 (d, J=8.5, 2H), 6.94 (d, J=8.4, 2H), 2.72-2.49 (m, 6H), 1.72-1.64 (m, 1H), 1.26-1.16 (m, 1H), 1.07 (t, J=7.1, 6H), 0.96 (dt, J=8.5, 5.1, 1H), 0.88 (dt, J=8.5, 5.1, 1H). $^{13}$C NMR (101 MHz, CDCL$_3$) δ 141.87, 130.91, 127.05, 118.58, 56.95, 46.82, 22.42, 21.62, 15.52, 11.96. MS (ESI+) 282, 284 (M+H).

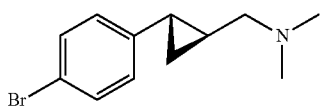

7d

1-((1S,2S)-2-(4-bromophenyl)cyclopropyl)-N,N-dimethylmethanamine (7d)

Following the general procedure, reaction of 6d (3.22 g assayed, 12.0 mmol) with 1 M $BH_3$ in THF (42.0 mL, 42.0 mmol) afforded 7d in an assayed yield of 2.21 g (8.7 mmol, 73% assay yield, 99% peak area). A sample was concentrated in vacuo to an oil to provide the standard.

$^1$H NMR (400 MHz, $CDCL_3$) δ 7.38 (d, J=8.4, 2H), 6.96 (d, J=8.4, 2H), 2.45 (dd, J=12.5, 6.2, 1H), 2.32 (s, 6H), 2.29 (dd, J=12.5, 6.9, 1H), 1.73-1.64 (m, 1H), 1.28-1.16 (m, 1H), 0.97 (dt, J=8.5, 5.1, 1H), 0.89 (dt, J=8.6, 5.4, 1H). $^{13}$C NMR (101 MHz, $CDCL_3$) δ 141.66, 130.94, 127.12, 118.67, 63.92, 45.60, 22.48, 22.10, 15.38. MS (ESI+) 254, 256 (M+H).

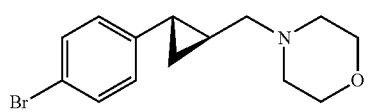

7e

4-(((1S,2S)-2-(4-bromophenyl)cyclopropyl)methyl)morpholine (7e)

Following the general procedure, reaction of 6e (4.20 g assayed, 13.55 mmol) with 1 M $BH_3$ in THF (47.4 mL, 47.4 mmol) afforded 7e in an assay yield of 2.68 g (9.05 mmol, 67% assay yield, 100% peak area). A sample was concentrated in vacuo to an oil to provide the standard.

$^1$H NMR (400 MHz, $CDCL_3$) δ 7.41-7.34 (m, 2H), 6.97-6.89 (m, 2H), 3.82-3.66 (m, 4H), 2.63-2.45 (m, 5H), 2.35 (dd, J=12.6, 7.0, 1H), 1.75-1.59 (m, 2H), 1.30-1.14 (m, 1H), 0.97 (dt, J=8.5, 5.1, 1H), 0.92-0.83 (m, 1H). $^{13}$C NMR (101 MHz, $CDCL_3$) δ 141.42, 131.02, 127.04, 118.79, 66.98, 63.34, 53.76, 22.56, 21.11, 15.43 MS (DCI+) 296, 298 (M+H).

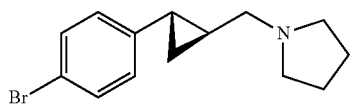

7f

1-(((1S,2S)-2-(4-bromophenyl)cyclopropyl)methyl)pyrrolidine (7f)

Following the general procedure, reaction of 6f (3.95 g assayed, 13.42 mmol) with 1 M $BH_3$ in THF (40.3 mL, 40.3 mmol) afforded 7f in an assay yield of 3.15 g (11.25 mmol, 84% assay yield, 100% peak area). A sample was concentrated in vacuo to an oil to provide the standard.

$^1$H NMR (400 MHz, $CDCL_3$) δ 7.41-7.34 (m, 2H), 6.98-6.89 (m, 2H), 2.65 (dd, J=12.3, 6.2, 1H), 2.58 (tt, J=4.4, 2.7, 4H), 2.39 (dd, J=12.3, 7.0, 1H), 1.86-1.73 (m, 4H), 1.73-1.61 (m, 1H), 1.36-1.22 (m, 1H), 1.02-0.84 (m, 2H). $^{13}$C NMR (101 MHz, $CDCL_3$) δ 141.78, 130.91, 127.11, 118.61, 60.50, 54.42, 23.67, 23.02, 22.45, 15.52. MS (DCI+) 280, 282 (M+H).

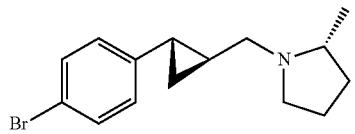

7g

(R)-1-(((1S,2S)-2-(4-bromophenyl)cyclopropyl)methyl)-2-methylpyrrolidine (7 g)

Following the general procedure, reaction of 6 g (4.35 g assayed, 14.10 mmol) with 1 M $BH_3$ in THF (42.3 mL, 42.3 mmol) afforded 7 g in an assayed yield of 3.44 g (11.70 mmol, 83% assay yield, 100% peak area). A sample was concentrated in vacuo to an oil to provide the standard.

$^1$H NMR (400 MHz, $CDCL_3$) δ 7.40-7.34 (m, 2H), 6.97-6.90 (m, 2H), 3.35-3.25 (m, 1H), 3.07 (dd, J=12.4, 5.5, 1H), 2.40-2.28 (m, 1H), 2.21 (dd, J=17.7, 9.0, 1H), 2.02-1.62 (m, 6H), 1.45 (dddd, J=12.1, 10.5, 8.4, 5.6, 1H), 1.36-1.23 (m, 1H), 1.13 (t, J=6.0, 3H), 0.94 (ddt, J=10.7, 8.6, 5.1, 2H). $^{13}$C NMR (101 MHz, $CDCL_3$) δ 141.95, 130.89, 127.10, 118.53, 59.69, 57.92, 54.49, 32.76, 22.52, 22.05, 21.22, 19.34, 17.06. MS (DCI+) 294, 296 (M+H).

Example 3c

Preparation of a Compound of Structure 8, Scheme 3

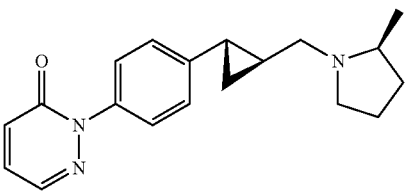

8a

2-(4-((1S,2S)-2-(amino)methyl)cyclopropyl)phenyl)pyridazin-3(2H)-one, L-tartrate monohydrate salt (8)

The solution of the bromophenyl 7a in EtOAc (14.5 g assayed, 49.2 mmol) was diluted with pyridine (75 mL) and distilled to ½ volume. N,N'-dimethylethylenediamine (20.1 mL, 19.7 mmol) was added and the solution sparged with $N_2$. Separately, added copper (I) iodide (1.87 g, 9.8 mmol), 3(2H)-pyridazinone (6.15 g, 63.9 mmol) and milled potassium carbonate (10.2 g, 73.8 mmol) to a reactor. Evacuated and purged with $N_2$ (3×). Added the solution of 6 and heated to reflux (~115° C.). The reaction mixture was monitored by HPLC for reaction completion (typically >16 h). The reaction mixture was cooled to room temperature. Added a 5% solution of ammonium hydroxide (200 mL) and extracted with toluene (300 mL). The aqueous layer was removed and the product, organic layer was distilled to ¼ volume. After chased with more toluene (150 mL), the product layer was extracted with 5% solution of ammonium hydroxide (100 mL, 2×) and then a 12% solution of sodium chloride (100 mL). The product layer was distilled to ¼ volume and chased with Isopropyl Alcohol (150 mL). The resulting product solution (~130 mL) was assayed by HPLC against a known standard. 13.1 g product was assayed (86% assayed yield, 98% peak area).

To the free base solution in isopropyl alcohol was charged a solution of L-tartaric acid in water (1.2 equivalents), at the inner temperature of 35° C. (concentration of the freebase was ~60 mg/g solution). The solvent composition was adjusted to ~17% water in isopropyl alcohol (by volume). The solution was cooled to 15° C., and seeded (1 percent calculated for the expected yield, without pretreatment) to induce crystallization. The slurry was held for 1 h, then reheated to 35° C. and held for 1 h to generate a seedbed. Controlled de-supersaturation was carried out by cooling the crystallization slurry to 15° C. over 10 h. The yield was increased by stepwise addition of isopropyl alcohol alternating with hold times over 10 h at 15° C., reducing the water content to 10% (by volume) in the final solvent composition. The solid was filtered and washed with isopropyl alcohol twice (4.5 mL/g free base). Wet cake was dried at 50° C. under vacuum, in humidified environment, with intermittent slight nitrogen bleeding. The isolated solid was used as a standard. $^1$H NMR (400 MHz, DMSO) δ 0.97-1.17 (m, 2H), 1.26 (d, J=6.4, 3H), 1.40-1.47 (m, 1H), 1.52-1.60 (m, 1H), 1.77-1.95 (m, 2H), 1.99-2.19 (m, 2H), 2.70-2.75 (m, 1H), 2.95-3.02 (m, 1H), 3.08-3.14 (m, 1H), 3.27-3.38 (m, 1H), 3.39-3.55 (m, 1H), 4.02 (s, 2H), 7.04 (dd, J=1.6, 9.5, 1H), 7.16-7.29 (m, 2H), 7.39-7.43 (m, 2H), 7.46 (dd, J=3.7, 9.5, 1H), 8.02 (dd, J=1.6, 3.8, 1H). $^{13}$C NMR (100 MHz, DMSO) δ 14.5, 16.2, 19.6, 21.1, 22.3, 31.2, 52.4, 55.3, 61.5, 71.7, 125.0, 125.3, 130.1, 131.8, 136.9, 138.7, 141.2, 158.7, 173.6 with 4 peaks overlapping.

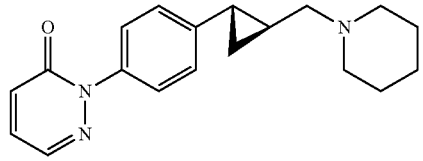

L-tartrate 2-(4-((1S,2S)-2-(piperidin-1-ylmethyl)cyclopropyl)phenyl)pyridazin-3(2H)-one (8b)

Following the general procedure, reaction of 7b (2.67 g assayed, 9.08 mmol) with 3(2H)-pyridazinone (1.14 g, 11.8 mmol) afforded a solution of the free base of 8b in an assayed yield of 2.61 g (93% assay yield, 95% peak area).

Formation of the L-(+)-tartaric acid salt gave 3.64 g (82% yield corrected for 5.8 wt % H$_2$O, 99% peak area) of 8b as a white solid which was used as a standard.

$^1$H NMR (400 MHz, DMSO) δ 8.01 (dd, J=3.8, 1.6, 1H), 7.46 (dd, J=9.5, 3.8, 1H), 7.41 (d, J=8.5, 2H), 7.20 (d, J=8.5, 2H), 7.03 (dd, J=9.5, 1.6, 1H), 4.01 (s, 2H), 3.05-2.88 (m, 5H), 2.83 (dd, J=12.9, 7.5, 1H), 2.04-1.94 (m, 1H), 1.72-1.61 (m, 5.4, 4H), 1.52-1.35 (m, 3H), 1.09 (dt, J=8.5, 5.1, 1H), 1.02 (dt, J=8.9, 5.1, 1H). $^{13}$C NMR (101 MHz, DMSO) δ 173.51, 158.65, 141.31, 138.65, 136.85, 131.79, 130.05, 125.23, 124.98, 71.61, 59.84, 51.99, 23.22, 22.22, 21.95, 18.42, 14.99. MS (ESI+) 310 (M+H).

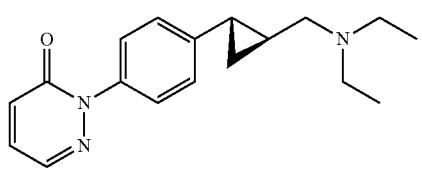

L-tartrate 2-(4-((1S,2S)-2-((diethylamino)methyl)cyclopropyl)phenyl)pyridazin-3(2H)-one (8c)

Following the general procedure, reaction of 7c (2.87 g assayed, 10.2 mmol) with 3(2H)-pyridazinone (1.27 g, 13.2 mmol) afforded a solution of the free base of 8c in an assayed yield of 2.55 g (84% assay yield, 93% peak area).

Formation of the L-(+)-tartaric acid salt gave 3.24 g (68% yield corrected for 4.9 wt % H$_2$O, 98% peak area) of 8c as a white solid which was used as a standard.

$^1$H NMR (400 MHz, DMSO) δ 8.02 (dd, J=3.8, 1.6, 1H), 7.46 (dd, J=9.5, 3.8, 1H), 7.41 (d, J=8.5, 2H), 7.21 (d, J=8.5, 2H), 7.03 (dd, J=9.5, 1.6, 1H), 3.98 (s, 2H), 3.12-2.90 (m, 6H), 2.09-2.01 (m, 1H), 1.46-1.35 (m, 1H), 1.15 (t, J=7.2, 6H), 1.12-1.00 (m, 2H). $^{13}$C NMR (101 MHz, DMSO) δ 173.57, 158.65, 141.23, 138.68, 136.85, 131.80, 130.05, 125.28, 124.97, 71.54, 54.47, 45.60, 21.81, 18.34, 14.86, 9.15. MS (ESI+) 298 (M+H).

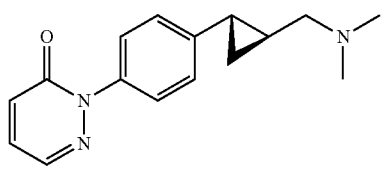

L-tartrate 2-(4-((1S,2S)-2-((dimethylamino)methyl)cyclopropyl)phenyl)pyridazin-3(2H)-one (8d)

Following the general procedure, reaction of 7d (2.13 g assayed, 8.37 mmol) with 3(2H)-pyridazinone (1.05 g, 10.5 mmol) afforded a solution of the free base of 8d in an assayed yield of 1.57 g (5.8 mmol, 70% assay yield, 93% peak area).

Formation of the L-(+)-tartaric acid salt gave 2.33 g (65% yield corrected for 2.7 wt % H$_2$O, 95% peak area) of 8d as a white solid which was used as a standard.

$^1$H NMR (400 MHz, DMSO) δ 8.01 (dd, J=3.8, 1.6, 1H), 7.46 (dd, J=9.5, 3.8, 1H), 7.41 (d, J=8.5, 2H), 7.22 (d, J=8.6, 2H), 7.03 (dd, J=9.5, 1.6, 1H), 4.02 (s, 2H), 3.01 (dd, J=12.9, 6.5, 1H), 2.85 (dd, J=12.0, 6.7, 1H), 2.62 (s, 6H), 2.07-1.97 (m, 1H), 1.47-1.31 (m, 1H), 1.11 (dt, J=8.5, 5.1, 1H), 1.03 (dt, J=5.1, 4.4, 1H). $^{13}$C NMR (101 MHz, DMSO) δ 173.67, 158.64, 141.20, 138.67, 136.85, 131.79, 130.05, 125.29, 124.95, 71.67, 60.16, 42.34, 21.76, 18.84, 14.69. MS (ESI+) 270 (M+H).

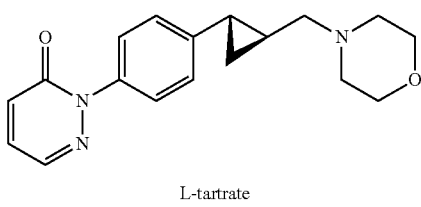

L-tartrate

2-(4-((1S,2S)-2-(morpholinomethyl)cyclopropyl)phenyl)pyridazin-3(2H)-one (8e)

Following the general procedure, reaction of 7e (2.59 g assayed, 8.75 mmol) with 3(2H)-pyridazinone (1.09 g, 11.37 mmol) afforded a solution of the free base of 8e in an assayed yield of 2.03 g (50% assay yield, 96% peak area).

Formation of the L-(+)-tartaric acid salt gave 1.96 g (49% yield, 100% peak area) of 8e as a white solid which was used as a standard.

$^1$H NMR (400 MHz, DMSO) δ 8.00 (dd, J=3.8, 1.6, 1H), 7.44 (dd, J=9.5, 3.8, 1H), 7.40-7.34 (m, 2H), 7.18-7.12 (m, 2H), 7.02 (dd, J=9.5, 1.6, 1H), 4.14 (s, 2H), 3.63-3.48 (m, 4H), 2.59 (dd, J=12.7, 5.7, 1H), 2.48 (dt, J=3.7, 1.9, 2H), 2.30 (dd, J=12.6, 7.4, 1H), 1.86-1.74 (m, 1H), 1.29-1.15 (m, 1H), 1.04-0.81 (m, 2H). $^{13}$C NMR (101 MHz, DMSO) δ 172.68, 158.65, 142.26, 138.41, 136.80, 131.75, 130.03, 124.97, 124.92, 71.59, 65.76, 62.02, 52.87, 22.12, 20.90, 14.93. MS (ESI+) 312 (M+H).

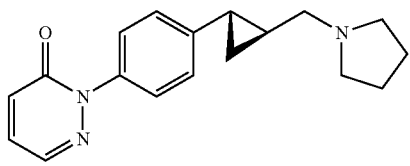

L-tartrate

2-(4-((1S,2S)-2-(pyrrolidin-1-ylmethyl)cyclopropyl)phenyl)pyridazin-3(2H)-one (8f)

Following the general procedure, reaction of 7f (3.05 g assayed, 10.90 mmol) with 3(211)-pyridazinone (1.36 g, 14.17 mmol) afforded a solution of the free base of 8f in an assayed yield of 3.60 g (74% assay yield, 97% peak area).

Formation of the L-(+)-tartaric acid salt gave 3.46 g (71% yield, 100% peak area) of 8f as a white solid which was used as a standard.

$^1$H NMR (400 MHz, DMSO) δ 8.00 (dd, J=3.8, 1.6, 1H), 7.45 (dd, J=9.5, 3.8, 1H), 7.42-7.36 (m, 2H), 7.23-7.16 (m, 2H), 7.02 (dd, J=9.5, 1.6, 1H), 3.96 (s, 2H), 3.11 (dd, J=12.9, 6.4, 3H), 2.91 (dd, J=12.7, 7.7, 1H), 2.09-1.98 (m, 1H), 1.85 (t, J=6.5, 4H), 1.50-1.33 (m, 1H), 1.14-0.96 (m, 2H). $^{13}$C NMR (101 MHz, DMSO) δ 173.40, 158.68, 141.33, 138.66, 136.86, 131.80, 130.05, 125.29, 124.96, 71.28, 57.54, 52.84, 22.76, 21.79, 20.12, 14.69. MS (ESI+) 296 (M+H).

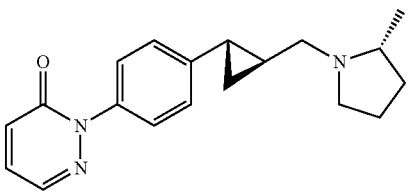

L-tartrate

2-(4-((1S,2S)-2-(((R)-2-methylpyrrolidin-1-yl)methyl)cyclopropyl)phenyl)pyridazin-3(2H)-one (8 g)

Following the general procedure, reaction of 7 g (3.34 g assayed, 11.34 mmol) with 3(2H)-pyridazinone (1.42 g, 14.75 mmol) afforded a solution of the free base of 8 g in an assayed yield of 3.85 g (74% assay yield, 97% peak area).

Formation of the L-(+)-tartaric acid salt gave 3.56 g (68% yield, 99% peak area) of 8 g as a white solid which was used as a standard.

$^1$H NMR (400 MHz, DMSO) δ 8.00 (dd, J=3.8, 1.6, 1H), 7.45 (dd, J=9.5, 3.8, 1H), 7.42-7.36 (m, 2H), 7.23-7.17 (m, 2H), 7.02 (dd, J=9.5, 1.6, 1H), 3.96 (s, 2H), 3.47-3.35 (m, 1H), 2.90 (d, J=10.2, 1H), 2.86-2.75 (m, 1H), 2.12-2.03 (m, 1H), 2.03-1.97 (m, 1H), 1.93-1.74 (m, 2H), 1.62-1.47 (m, 1H), 1.47-1.34 (m, 1H), 1.22 (d, J=6.4, 3H), 1.12-0.98 (m, 2H). $^{13}$C NMR (101 MHz, DMSO) δ 173.44, 158.70, 141.41, 138.65, 136.88, 131.82, 130.07, 125.35, 124.94, 71.44, 61.36, 55.38, 52.46, 31.23, 21.38, 21.17, 19.54, 16.41, 15.50. MS (ESI+) 310 (M+H).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A process for preparing a chiral compound of formula:

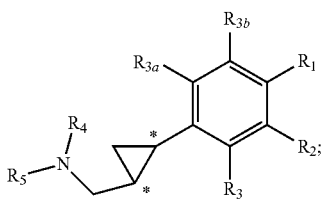

(II)

wherein $R_2$, $R_3$, $R_{3a}$, and $R_{3b}$, are hydrogen; $R_1$ is a 5- to 6-membered heteroaryl ring, cyanophenyl, a 8- to 12-membered bicyclic heteroaryl ring, or a 4- to 12-membered heterocyclic ring; and $R_4$ and $R_5$ taken together with the nitrogen atom to which they are attached form an amine moiety represented by structure:

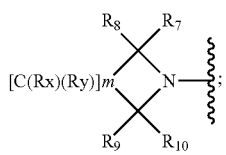

(II-a)

wherein $R_7$, $R_8$, $R_9$, and $R_{10}$ at each occurrence are independently selected from the group consisting of hydrogen, hydroxyalkyl, fluoroalkyl, cycloalkyl, and alkyl; $R_x$ and $R_y$ are each independently selected from the group consisting of hydrogen, hydroxy, alkyl, alkoxy, alkylamino, fluoro, and dialkylamino; and m is an integer from 1 to 5;

comprising the steps of:

a) providing enantiomerically pure chiral salts using chiral resolution with a chiral amine:

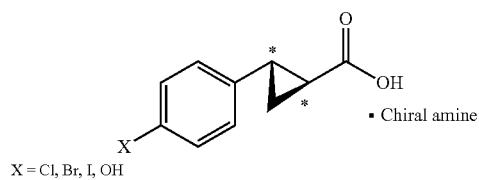

wherein the chiral amine is selected from the group consisting of R-(−)-1-cyclohexylethylamine, (R)-(+)-α-methylbenzylamine, (S)-(−)-α-methylbenzylamine, (R)-(+)-N-benzyl-α-methylbenzylamine, (S)-(−)-N-benzyl-α-methylbenzylamine, (R)-(+)-N,N-dimethyl-1-phenylethylamine, (S)-(−)-N,N-dimethyl-1-phenylethylamine, [R-(R*,R*)]-(+)-bis(α-methylbenzyl)amine, [S-(R*,R*)]-(−)-bis(α-methylbenzyl)amine, (S)-(+)-1-cyclohexylethylamine, (R)-(+)-1-(1-naphthyl)ethylamine, (S)-(−)-1-(1-naphthyl)ethylamine, (1R,2R,3R,5S)-(−)-isopinocamphenylamine, (1S,2S,3S,5R)-(+)-isopinocamphenylamine, (1R2R)-(−)-pseudoephedrine, (1S,2S)-(+)-pseudoephedrine, (1R,2S)-(−)-ephedrine, (1S,2R)-(+)-ephedrine, (1R,2S)-(−)-N-methylephedrine, (1S,2R)-(+)-N-methylephedrine, (1R,2S)-(−)-norephedrine, (1S,2R)-(+)-norephedrine, (1R,2S)-(+)-cis-1-amino-2-indanol, (1S,2R)-(−)-cis-1-amino-2-indanol, quinine, and cinchonine;

b) reacting the chiral pure arylcyclopropanecarboxylic acid after released from the chiral salt obtained from chiral resolution with an amine of formula:

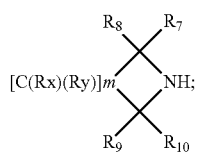

(a)

wherein $R_7$, $R_8$, $R_9$, and $R_{10}$ at each occurrence are independently selected from the group consisting of hydrogen, hydroxyalkyl, fluoroalkyl, cycloalkyl, and alkyl; $R_x$ and $R_y$ are each independently selected from the group consisting of hydrogen, hydroxy, alkyl, alkoxy, alkylamino, fluoro, and dialkylamino; and m is an integer from 1 to 5; and N,N'-carbonyldiimidazole in tetrahydrofuran to provide a chiral compound of structure:

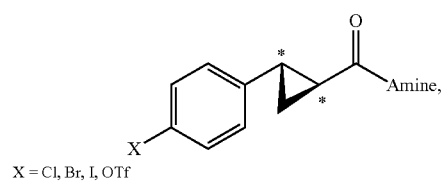

(I-a)

X = Cl, Br, I, OTf wherein X is chloro, bromo, iodo, or trifluoromethanesulfonate, and the amine moiety in the structure above is represented by:

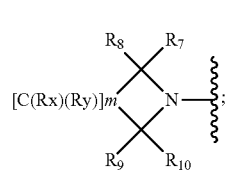

(II-a)

wherein $R_7$, $R_8$, $R_9$, and $R_{10}$ at each occurrence are independently selected from the group consisting of hydrogen, hydroxyalkyl, fluoroalkyl, cycloalkyl, and alkyl; $R_x$ and $R_y$ are each independently selected from the group consisting of hydrogen, hydroxy, alkyl, alkoxy, alkylamino, fluoro, and dialkylamino; and m is an integer from 1 to 5;

c) reducing the product of step b to provide a compound of structure:

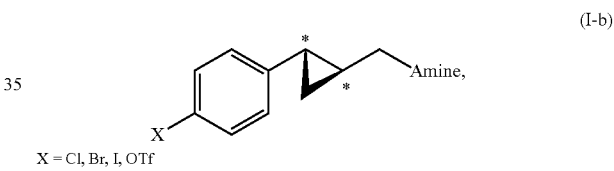

(I-b)

X = Cl, Br, I, OTf wherein X and the amine moiety are as described above for compounds of step b); and d) treating the product of step c with a reagent selected from the group consisting of 5- to 6-membered heteroaryl, 8- to 12-membered bicyclic heteroaryl, 4- to 12-membered heterocycloalkyl, N,N'-dimethylethylenediamine, a copper catalyst, and base, in a basic solvent; to provide a compound of formula (II).

2. The process of claim 1, the chiral amine is R-(−)-1-cyclohexylethylamine and (R)-(+)-α-methylbenzylamine.

3. The process of claim 1, wherein the amine of formula (a) in step b) is pyrrolidine, 2-R-methylpyrrolidine, 2-S-methylpyrrolidine, or 3-methylpyrrolidine.

4. The process of claim 1, wherein the compound of structure (1-a) is reduced using borane.

5. The process of claim 4, wherein the borane reagent is borane or diborane.

6. The process of claim 1, wherein the compound of structure (I-a) is reduced using borane in a polar solvent.

7. The process of claim 6, wherein the polar solvent is tetrahydrofuran.

8. The process of claim 6, wherein the non-polar solvent is toluene.

9. The process of claim 1, wherein the copper catalyst in step d) is copper (I) iodide.

10. The process of claim 1, wherein the copper catalyst in step d) is copper (I) bromide or copper (I) chloride.

11. The process of claim 1, wherein the base in step d) is potassium carbonate ($K_2CO_3$).

12. The process of claim 1, wherein the base in step d) is potassium phosphate ($K_3PO_4$).

13. The process of claim 1, wherein the base is step d) is cesium carbonate (Cs₂CO₃), sodium methoxide (NaOMe), sodium tert-butoxide (NaOt-Bu), sodium acetate (NaOAc), potassium tert-butoxide (KOt-Bu).

14. The process of claim 1, wherein the polar aprotic solvent in step d) is pyridine.

15. The process of claim 1, wherein the polar aprotic solvent in step d) is dimethyl acetamide, dimethyl formamide, or 1-methyl-2-pyrrolidinone.

16. A compound of formula:

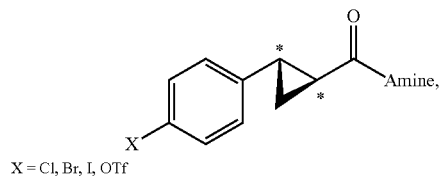

(I-a)

X = Cl, Br, I, OTf wherein the amine moiety in the structure above is represented by:

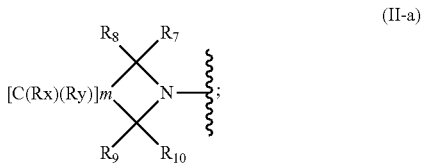

(II-a)

wherein $R_7$, $R_8$, $R_9$, and $R_{10}$ at each occurrence are independently selected from the group consisting of hydrogen, hydroxyalkyl, fluoroalkyl, cycloalkyl, and alkyl; $R_x$ and $R_y$ are each independently selected from the group consisting of hydrogen, hydroxy, alkyl, alkoxy, alkylamino, fluoro, and dialkylamino; and m is an integer from 1 to 5.

* * * * *